US011427646B2

(12) United States Patent
Cuvillier et al.

(10) Patent No.: US 11,427,646 B2
(45) Date of Patent: Aug. 30, 2022

(54) ANTIBODIES AGAINST CARCINOEMBRYONIC ANTIGEN FOR CANCER THERAPY AND DIAGNOSIS

(71) Applicant: B Cell Design, Limoges (FR)

(72) Inventors: Armelle Cuvillier, Saint-Jouvent (FR); Gaël Champier, Veyrac (FR)

(73) Assignee: B CELL DESIGN, Limoges (FR)

( * ) Notice: Subject to any disclaimer, the term of this patent is extended or adjusted under 35 U.S.C. 154(b) by 187 days.

(21) Appl. No.: 16/609,878

(22) PCT Filed: May 3, 2018

(86) PCT No.: PCT/EP2018/061385
§ 371 (c)(1),
(2) Date: Oct. 31, 2019

(87) PCT Pub. No.: WO2018/202794
PCT Pub. Date: Nov. 8, 2018

(65) Prior Publication Data
US 2020/0055952 A1 Feb. 20, 2020

(30) Foreign Application Priority Data

May 4, 2017 (EP) .................................... 17305498

(51) Int. Cl.
*C07K 16/30* (2006.01)
*A61P 35/00* (2006.01)
*A61K 45/06* (2006.01)
(52) U.S. Cl.
CPC .......... *C07K 16/3007* (2013.01); *A61P 35/00* (2018.01); *A61K 45/06* (2013.01); *C07K 2317/30* (2013.01); *C07K 2317/565* (2013.01)
(58) Field of Classification Search
CPC ............ C07K 16/3007; C07K 2317/30; C07K 2317/565
See application file for complete search history.

(56) References Cited

FOREIGN PATENT DOCUMENTS

WO 2013/012414 A1 1/2013

OTHER PUBLICATIONS

Lloyd et al.,Modelling the human immune response: performance of a 1011 human antibody repertoire against a broad panel of therapeutically relevant antigens. Protein Engineering, Design & Selection 2009, 22:159-168; (Year: 2009).*
Hart et al., "Human Cell Lined-Derived Monoclonal IgA Antibodies for Cancer Immunotherapy," Bioengineering, 4: 42 (2017).
Koga et al., "Mouse-Human Chimeric Monoclonal Antibody to Carcinoembryonic Antigen (CEA): In Vitro and In Vivo Activities," Hybridoma, 9: 43-56 (1990).
Zhao et al., "Recombinant Human Monoclonal IgA Antibody Against CEA to Recruit Neutrophils to CEA-Expressing Cells," Oncology Research, 17: 217-222 (2008).
Rognum et al., "Immunohistochemical Study of Secretory Component, Secretory IgA and Carcinoembryonic Antigen in Large Bowel Carcinomas," Pathology: Research and Practice, 170: 126-145 (1980).
Terskikh et al., "Dimeric Recombinant IgA Directed Against Carcino-Embryonic Antigen, A Novel Tool for Carcinoma Localization," Molecular Immunology, 31: 1313-1319 (1994).
Govindan et al., "CEACAM5-Targeted Therapy of Human Colonic and Pancreatic Cancer Xenografts with Potent Labetuzumab-SN-38 Immunoconjugates," Clinical Cancer Research, 15: 6052-6061 (2009).
Shibaguchi et al., "cDNA Cloning and Sequencing of a Novel Monoclonal Antibody to Carcinoembryonic Antigen and Construction of a Mouse/Human Chimeric Antibody," Anticancer Research, 23: 4383-4388 (2003).
Senba et al., "Tumor Growth Suppression by a Mouse/Human Chimeric Anti-CEA Antibody and Lymphokine-Activated Killer Cells in Vitro and in SCID Mouse Xenograft Model," Anticancer Research, 18: 17-24 (1998).
Kim-Schulze et al., "Intrarectal Vaccination with Recombinant Vaccinia Virus Expressing Carcinoembronic Antigen Induces Mucosal and Systemic Immunity and Prevents Progression of Colorectal Cancer," The Journal of Immunology, 181: 8112-8119(2008).
Sahlmann et al., "Repeated Adjuvant Anti-CEA Radioimmunotherapy After Resection of Colorectal Liver Metastases Safety, Feasibility, and Long-Term Efficacy Results of a Prospective Phase 2 Study," Cancer, 123: 638-649 (2016).
International Search Report issued in corresponding International Patent Application No. PCT/EP2018/061385 dated Jul. 11, 2018.
Written Opinion issued in corresponding International Patent Application No. PCT/EP2018/061385 dated Jul. 11, 2018.

* cited by examiner

*Primary Examiner* — Elly-Gerald Stoica
(74) *Attorney, Agent, or Firm* — Morgan, Lewis & Bockius LLP

(57) ABSTRACT

The invention relates to antibodies against carcinoembryonic antigen (CEA) which have a direct cell growth inhibition activity on tumor cells expressing CEA and to their use for the treatment and diagnosis of cancer.

Figure 1:
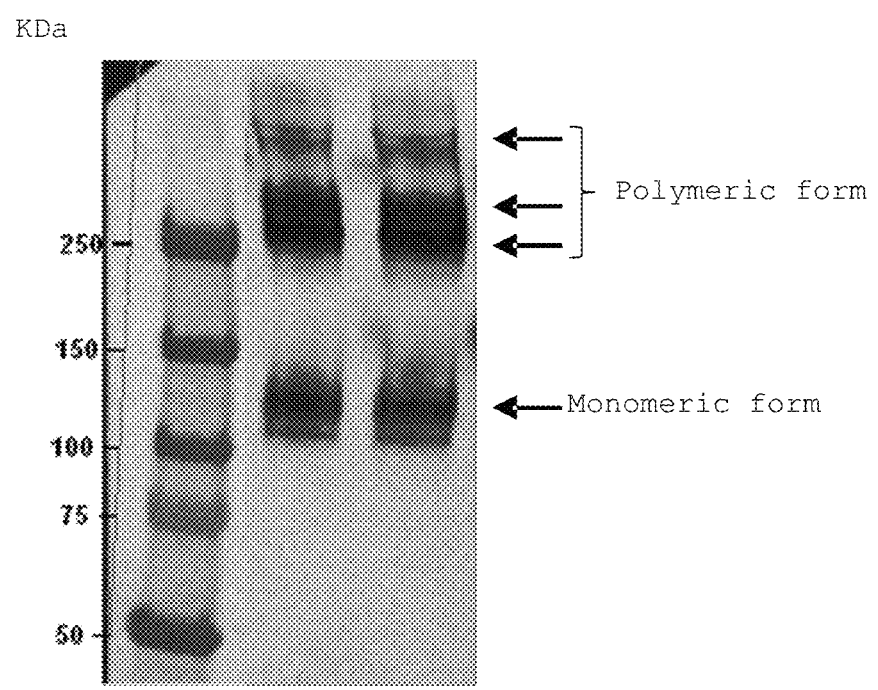

15 Claims, 8 Drawing Sheets
Specification includes a Sequence Listing.

A

B

A

B

ANTIBODIES AGAINST CARCINOEMBRYONIC ANTIGEN FOR CANCER THERAPY AND DIAGNOSIS

SEQUENCE LISTING SUBMISSION VIA EFS-WEB

A computer readable text file, entitled "SequenceListing.txt" created on or about Oct. 31, 2019 with a file size of about 9 kb contains the sequence listing for this application and is hereby incorporated by reference in its entirety.

The invention relates to antibodies against carcinoembryonic antigen (CEA) which have a direct tumor cell growth inhibition activity and to their use for the treatment and diagnosis of cancer.

Carcinoembryonic antigen (CEA or CEACAM-5) is a tumor associated antigen of the carcinoembryonic antigen-related cell adhesion molecule (CEACAM) family. CEACAM is a large, highly conserved gene family comprising 12 molecules with diverse functions in cell adhesion, in intracellular and intercellular signaling, and during complex biological processes such as cancer progression, inflammation, angiogenesis and metastasis (Reviewed in Beauchemin, M and Arabzadeh A, Cancer Metastasis Rev., 2013, 32, 643-671). All CEACAM proteins are highly glycosylated proteins, which belong to the immunoglobulin (Ig) supergene family and have a similar structure. CEACAM5 comprises one variable (V)-like domain, identified as the N domain, followed by three repeating units comprising, in total, six constant C2-like domains, and is associated with the membrane through a glycosylphosphatidylinositol (GPI) linkage.

CEA is considered a valid clinical biomarker and promising therapeutic target for various cancers. During malignant transformation, CEA is detected in at least carcinomas of lung (including small cell lung cancer), pancreas, gallbladder, urinary bladder, mucinous ovarian and endometrium and CEA is significantly over-expressed in a variety of mucosal epithelium cancers, such as colorectal (CRC), breast and gastric cancer.

Therefore, the development of anti-CEA monoclonal antibodies (MAbs) able to target efficiently tumor cells for cancer diagnosis and treatment has been actively pursued.

$^{99m}$Tc arcitumomab (CEA-Scan) is a F(ab')$_2$ fragment of IMMU-4 a murine IgG1 monoclonal antibody anti-CEA, labelled with 99m-technetium, which is marketed by Immunomedics for single photon emission computed tomography (SPECT) diagnosis imaging of colorectal cancers. CEA-Scan was shown suitable for the diagnosis of local recurrence of colorectal carcinoma but not suitable for the detection of distant metastases (liver, bone and lung) and lymph node involvement (Willkomm et al., J. Nucl. Med., 2000, 41, 1657-1663).

IMMU-130 (hMN14-SN38 or Labetuzumab-SN38; Govindan et al., Clin. Cancer Res., 2009, 15, 6052-6061), an antibody-drug conjugate targeting CEA is currently being tested in a phase I/II trial. $^{131}$I-labetuzumab has been tested in adjuvant radioimmunotherapy of colorectal cancer liver metastases (Sahlmann et al., Cancer, Feb. 15, 2017, 123, 638-649).

Several bispecific Abs targeting CEA and T-cells have been disclosed (WO 2013/012414) and are in preclinical trials (Bacac et al., Clin. Cancer Res., 2016, 22, 3286-; Weidle et al., Seminars in Oncology, 2014, 41, 653-660).

WO 92/01059 (CELLTECH LIMITED) discloses recombinant humanized or chimeric anti-CEA antibody derived from the anti-CEA mouse Mab A5B7 which has a binding affinity to CEA that is not substantially adversely affected by the humanization process.

U.S. Pat. No. 8,771,690 discloses human, humanized or chimeric anti-CEA monoclonal antibodies (MAbs) attached to human IgG1 or IgG4 constant region sequences which bind to CEA and CEACAM6 and inhibit the adhesion of tumor cells to endothelial cells.

Anti-CEA MAb were considered potential candidates for cytotoxic therapy against cancer since they killed CEA-expressing tumor cells via Antibody-dependent-cellular-cytotoxicity (ADCC) by recruiting immune effector cells expressing Ig Fc receptor (FcR), including IgG FcR (Fc-gammaR) and IgA FcR (Fc-alphaR) or via Complement Dependent Cytotoxicity (CDC; Staff et al., J. Clin. Immunol., 2012, 32, 855-865; Zhao et al., Oncol. Res., 2008, 17, 217-222). Recombinant human monoclonal IgA anti-CEA and mouse-human chimeric anti-CEA antibodies were derived from mouse anti-CEA monoclonal antibodies (Shibaguchi et al., Anticancer research, 2003, 23, 4883-4888; Senba et al., Anticancer research, 1998, 18, 17-24; Koga et al., Hybridoma, 1990, 9, 43-56).

A recombinant dimeric mouse-human IgA anti-CEA was constructed and shown to translocate in vitro across a monolayer of epithelial cells expressing the polyIg receptor (Terskikh et al., Molecular Immunology, 1994, 31, 1313-1319).

Despite these efforts, mucosal epithelium cancer diagnosis and treatment is still difficult since one in two patients diagnosed with CRC suffers already from liver and lung metastasis. Colorectal cancer is the second cancer, in terms of frequency, in women (after the breast cancer) and the third in men (after the lung cancer and of the prostate). Colonic cancers have a high frequency in France: every day, 100 people learn that they have colorectal cancer. Today, in the case of colorectal cancer, too few therapeutic molecules directly target a marker expressed on cancer cells. Approximately 30-50% of colorectal tumors are known to have a mutated (abnormal) KRAS gene, indicating that only 30% of patients with colorectal cancer (CRC) will respond to first-line conventional chemotherapy. Plus, 50% of patients who respond well to tyrosine kinase Inhibitors develop resistance due to the occurrence of secondary mutations. Monoclonal antibody (Cetuximab; ERBITUX®) targeting the epidermal growth factor receptor (EGFR) and vascular endothelial growth (VEGFr) factor is the gold standard in the current CRC immunotherapy treatment. However, only 50% of patients might respond to (Cetuximab, ERBITUX®) therapy and 40-60% of cetuximab-eligible patients do not respond to such therapy. Even if different treatment lines are available on the market, a significant proportion of patients cannot be treated effectively. Therefore, to improve early detection and treatment of mucosal epithelium cancers, there is a need for anti-CEA antibodies that can achieve an early and efficient targeting of mucosal epithelium tumors including primary tumors and metastasis.

Presently, IgG is the most widely used antibody in therapy and clinical trials. Intensively studied for many years, IgG is well known for inducing cellular cytotoxicity functions via the various receptors FcgammaR (FcγR).

However, some functional limitations of IgG, such as inadequate tissue accessibility and pharmacokinetics, and impaired interactions with effector cells, have been highlighted. IgA could represent a promising alternative to IgG, particularly to target mucosal tumours, considering that IgA constitutes the major Ig class at the mucosal surface.

In humans, IgA is the most heavily produced isotype (66 mg/kg/day) and the second-most prevalent circulating isotype, after IgG. Long regarded as an anti-inflammatory antibody involved in maintaining homeostatic balance at the level of the mucous membrane, it has been demonstrated recently that IgA can enable or inhibit different inflammatory responses. IgA is expressed in three different forms: monomeric (in the blood; 1 to 3 g/L), dimeric/polymeric (in mucous membranes) and secretory (in the mucosal organs). Although monomeric IgA is predominantly concentrated in blood and produced by bone marrow plasma cells, dimeric IgA are preferentially expressed in the lamina propria. This dimerization requires a 15-kDa joining (J) chain covalently bind to tailpiece of two IgA. The J chain in the IgA dimer is critical for its transport onto mucosal surfaces, because it mediates the recognition by the polymeric Ig receptor (pIgR) on the basolateral surface of epithelial cells allowing the IgA binding. After endocytotic internalization and transcytosis, pIgR is cleaved at the luminal surface, the extracellular loop of the receptor remains covalently linked to the dimer, releasing secretory IgA.

Knowledge of IgA and its applications is limited partly due to difficulties in the identification of IgA-producing B cells, and with respect to stable production of IgA antibodies. IgA-secreting B lymphocytes represent less than 1% of normal mouse splenocytes (even fewer are found in mucosal lymphoid compartments: 0.01% in the lamina propria and 0.1% in Peyer's patches). The recently developed HAMIGA™ technology allows this limitation to be bypassed (EP patent 1 680 449 B1). By replacing the Sμ domain with a human alpha 1 constant gene downstream of variable gene segments, the population of IgA-secreting lymphocytes B in the spleen was increased significantly and could thus easily generate highly specific, monoclonal humanised IgA.

The inventors have produced IgA antibodies against CEA using the HAMIGA™ technology. Surprisingly, they have found anti-CEA antibodies which have a direct cancer cell growth inhibition activity on cancer cells expressing CEA. This activity is present at least in IgA and IgG antibodies. This unique antitumor effect is further enhanced by the ability of the anti-CEA antibodies to recruit the complement pathway and the immune cell-effectors of antibody dependent cell cytotoxicity (ADCC) leading to cancer cell lysis. All these antitumor effects are specific for the targeted tumor cells because the antibodies are specific for CEA.

Using an orthotopic model of human colorectal cancer, the inventors have shown that these anti-CEA antibodies (IgA) have a fast and strong targeting power for the primary tumor and early metastasis (before macroscopic detection) that could prevent efficiently tumor growth in a mucosal environment. The antitumoral effect of the anti-CEA IgA antibodies in orthotopic model of human colorectal cancer was superior to that of anti-EGFR IgG antibody (cetuximab), the gold standard treatment for advanced colorectal cancer immunotherapy. These results support the potential of these anti-CEA antibodies for the diagnostic and treatment of mucosal tumors.

Therefore, the invention relates to an anti-CEA antibody which has a direct tumor cell growth inhibition activity on tumor cells expressing CEA.

As demonstrated in the examples of the present application, the antibody of the invention alone (i.e., isolated antibody) is capable of inhibiting the proliferation of tumor cells expressing CEA by directly inducing apoptosis in targeted tumor cells. In particular, the antibody of the invention is effective in the absence of immune effector cells that mediate Antibody-Dependent Cellular Cytotoxicity (ADCC) or Complement-Dependent Cellular cytotoxicity (CDC) or cytotoxic agent, conjugated (immunoconjugate approach) to the antibody or not conjugated to the antibody (complement or other free cytotoxic molecules).

The experimental data provided in the examples show that binding of the anti-CEA antibody of the invention to CEA expressed on tumor cells directly activates apoptotic signaling in targeted tumor cells. Without being bound by theory, it is considered that the direct antiproliferative effect of the anti-CEA antibody of the invention is mediated by its variable Fab regions. This is in contrast with ADCC and CDC which are indirect antibody-mediated target cell killing mechanisms which require interaction of antibodies constant regions with complement proteins or Fc receptors on immune effector cells such as natural killer (NK) cells, monocytes, macrophages and polynuclear cells.

In addition to having a direct cell growth inhibitory effect on tumor cells expressing CEA, the antibody of the invention also exhibits ADCC and CDC in the presence of immune effectors having complement proteins or Fc receptors on their surface.

The cancer cell growth inhibitory activity of the antibody of the invention may be measured on tumor cells expressing CEA using standard in vitro assays such as with no limitations: MTT, LDH leakage, total cellular protein measurement, neutral red, alamarBlue® or uridine incorporation assay. Alternatively or in addition, induction of apoptosis by the antibody of the invention directly in tumor cells expressing CEA may be assayed by detection of apoptosis markers such as phosphatidylserine exposure, caspase, calpain and cathepsin activation, changes in mitochondrial transmembrane potential, cell membrane blebbing and nuclear condensation, using conventional techniques that are available in the art.

According to the invention "antibody" refers to "isolated antibody". An Antibody refers to a glycoprotein produced by B cells in response to stimulation with an immunogen. Antibodies possess the ability to react in vitro and in vivo specifically and selectively with an antigenic determinant or epitope eliciting their production or with an antigenic determinant closely related to the homologous antigen.

In the present invention, the terms "antibody" and "immunoglobulin" are equivalent and used indifferently. Antibody is designated "Ab" and immunoglobulin is designated "Ig". The expressions "anti-CEA antibody", "antibody to CEA", "antibody against CEA", "antibody directed against CEA" or "antibody directed to CEA" are equivalent and used indifferently. "CEA" refers to CEA protein. The CEA protein is also designated CEA antigen.

According to the invention, the anti-CEA antibody recognizes specifically CEA. This means that the antibody according to the invention has a relatively high affinity to one or more epitopes of CEA, but do not substantially recognize and bind to peptides other than the one(s) of interest. As used herein, the term "relatively high affinity" means a binding affinity between the antibody and the protein of interest of at least $10^{-6}$ M, and preferably of at least about $10^{-7}$ M and even more preferably $10^{-8}$ M to $10^{-10}$ M. Determination of such affinity is preferably conducted under standard competitive binding immunoassay conditions which is common knowledge to the person of ordinary skill in the art.

An antibody according to the invention may comprise a whole antibody or antigen-binding fragment thereof. The antibody fragment may be selected from the group consisting of: Fv, ScFv, Fab, F(ab)$_2$, Fab' fragments and single domain antibodies (VHH). The constant region domains may be IgA, IgM, IgE, IgG or IgD domains. The antibody may be monoclonal or polyclonal, non-recombinant or recombinant, chimeric or humanized. A monoclonal antibody is a monospecific and bivalent immunoglobulin molecule. The term "antibody" is meant to encompass an aggregate, polymer, derivative, or conjugate of antibody or antibody fragment. Examples of derivative include variants and constructions using the antigen-binding fragment of such an antibody such as multivalent and/or multispecific antibodies.

The CEA antigen is well-known in the art; nucleotide and protein coding sequences for CEA are available in public sequence data bases. For example, human CEA amino acid sequence is available under GenBank AAA51967.1, GenBank AAA62835.1 or UniProtKB/Swiss-Prot: P06731.3.

In some embodiments, said antibody is a monoclonal antibody (mAb), preferably human, humanized or chimeric. A chimeric antibody has human constant domains and variable domains from a non-human source, generally mouse (human/mouse chimeric antibody). A more preferred antibody of the invention is a human/mouse chimeric monoclonal antibody.

In some embodiments, said antibody comprises light-chain (VL) and heavy-chain (VH) variable domains complementarity-determining region (CDR) sequences selected from the group consisting of:

a) the VL-CDR1 sequence: QTIGTR (SEQ ID NO: 1); the VL-CDR2 sequence: AAT; the VL-CDR3 sequence: QQLYSTPYT (SEQ ID NO: 2); the VH-CDR1 sequence: GYTFTNYG (SEQ ID NO: 3); the VH-CDR2 sequence: INTNTGEP (SEQ ID NO: 4); and the VH-CDR3 sequence: ARLWYLYFDV (SEQ ID NO: 5), which are the CDR sequences of the monoclonal antibody mAb 15B3 disclosed in the examples of the present application;

b) the VL-CDR1 sequence: QSFSNN (SEQ ID NO: 6); the VL-CDR2 sequence: YAS; the VL-CDR3 sequence: QQSNSWPLT (SEQ ID NO:7); the VH-CDR1 sequence: GYTFTNYG (SEQ ID NO: 8); the VH-CDR2 sequence: INTNTGEP (SEQ ID NO: 9); and the VH-CDR3 sequence: ARLWYLYFDV (SEQ ID NO: 10), which are the CDR sequences of the monoclonal antibody mAb 14G8 disclosed in the examples of the present application;

c) VL-CDR1, VL-CDR2, VL-CDR3, VH-CDR1, VH-CDR2 and VH-CDR3 sequences which differ from the sequences AAT and SEQ ID NO: 1 to 5 or the sequences YAS and SEQ ID NO: 6 to 10 by no more than 3 amino acid differences (1, 2 or 3 amino acid differences) in at least one of said sequences, preferably 1 or 2 amino acid differences, and wherein the antibody comprising said sequence variants recognizes specifically the CEA antigen and has direct cell growth inhibitory activity on tumor cells expressing the CEA antigen.

Preferably, the six CDR sequences in c) altogether do not comprise more than 6 amino acid differences (i.e. 1, 2, 3, 4, 5 or 6 amino acid differences) in the sequences AAT, YAS and SEQ ID NO: 1 to 10.

In some embodiments, the amino acid differences are conservative substitutions, i.e., substitutions of one amino acid with another having similar chemical or physical properties (size, charge or polarity), which substitution generally does not adversely affect the biochemical, biophysical and/or biological properties of the antibody. In particular, the substitution does not disrupt the interaction of the antibody with the CEA antigen. Said conservative substitution(s) are advantageously chosen within one of the following five groups: Group 1-small aliphatic, non-polar or slightly polar residues (A, S, T, P, G); Group 2-polar, negatively charged residues and their amides (D, N, E, Q); Group 3-polar, positively charged residues (H, R, K); Group 4-large aliphatic, nonpolar residues (M, L, I, V, C); and Group 5-large, aromatic residues (F, Y, W).

In some embodiments, said antibody has a variable region formed by the association of a VL domain comprising or consisting of SEQ ID NO: 11 and a VH domain comprising or consisting of SEQ ID NO: 12 such as the monoclonal antibody 15B3 or by a VL domain comprising or consisting of SEQ ID NO: 13 and a VH domain comprising or consisting of SEQ ID NO: 14 such as the monoclonal antibody 14G8.

In some embodiments, said antibody binds to the epitope bound by the antibody having the VH-CDR and VL-CDR sequences as defined above. Preferably, said antibody binds to the epitope bound by a monoclonal antibody having a variable region formed by the association of a VL domain comprising or consisting of SEQ ID NO: 11 and a VH domain comprising or consisting of SEQ ID NO: 12 such as the monoclonal antibody 15B3 or by a VL domain comprising or consisting of SEQ ID NO: 13 and a VH domain comprising or consisting of SEQ ID NO: 14 such as the monoclonal antibody 14G8.

In some embodiments, said antibody is an IgG or IgA, preferably an IgA.

In some embodiments, said antibody is polymeric. The polymeric antibody comprises or consists of Ig polymers. The polymeric antibody is preferably a polymeric monoclonal antibody derived from a monoclonal antibody as defined above. The Ig polymers comprise or consist of dimers. The polymeric antibody usually comprises immunoglobulin joining (J) chain(s) in addition to Ig molecules. The J chain is a 137 amino acid polypeptide expressed by plasma or myeloma cells which regulate Ig polymer formation by binding covalently to two Ig molecules through disulfide bonds between cysteine residues. In particular, dimeric antibodies are formed by two monomeric Ig molecules, which covalently bind to a J chain.

In a preferred embodiment, said antibody is a polymeric IgA, preferably a polymeric IgA monoclonal antibody derived from a monoclonal antibody as defined above.

In some embodiments the antibody is a secretory antibody. A secretory antibody can be transported across epithelial cells to the luminal surface of serosal tissues. The secretory antibody is usually a polymeric antibody, preferably a polymeric IgA, comprising a complex of J-chain-containing polymer of Ig and secretory component (SC). The secretory component is a proteolytic cleavage product of the extracellular part of the polymeric immunoglobulin receptor (pIgR) which binds to J-chain containing polymeric Ig. The secretory antibody is preferably a secretory monoclonal antibody derived from a monoclonal antibody as defined above.

The antibody of the invention may be directed against a CEA protein from any mammal. In some embodiments, said antibody is directed against human CEA.

In some embodiments, the antibody is specific for CEA and does not cross-react with other CEACAM molecule(s). In a preferred embodiment, the antibody does not cross-react with CEACAM6.

Examples of preferred antibodies according to the invention include:

a) a human/mouse chimeric monoclonal IgA antibody comprising:
(i) a light-chain variable domain (VL) having (i.e. comprising or consisting of) the sequence:

DIQMTQSPASQSASLGESVTITCLASQTIGTR-
LAWYQQKPGKSPQLLIYAATRLADGV
P.SRFSGSGSGTKFSFKISSLQAE-
DFVSYYCQQLYSTPYTFGGGTKLEIK (SEQ ID
NO: 11) and a heavy-chain variable domain (VH)
having (i.e. comprising or consisting of) the sequence:
QIQLVQSGPELKKPGETVKISCK-
ASGYTFTNYGMNWVNQAPGKGLKWMGWIN-
TNT GEPTYAEEFKGRFAFSLETSASTAY-
LQINNLKNEDTATYFCARLWYLYFDVWGAGTT
VTVSS (SEQ ID NO: 12), corresponding to mAb
15B3,
(ii) a light-chain variable domain (VL) having (i.e. comprising or consisting of) the sequence:
DIVLTQSPATLSVTPGDSVSLSCRASQSFSNNLH
WYQQKSHESPRLLIKYAAQSISGIPS
KFTGSGSGTDFTLSINSVETEDFGMYFCQQSN-
SWPLTFGAGTKLELK (SEQ ID NO: 13) and a
heavy-chain variable domain (VH) having the
sequence: QIQLVQSGPELKKPGETVKISCK-
ASGYTFTNYGMNWVNQAPGKGLKWMGWIN-
TNT GEPTYAEEFK.GRFAFSLETSASTAY-
LQINNLKNEDTATYFCARLWYLYFDVWGAGT
TVTVSS (SEQ ID NO: 14), corresponding to mAb
14G8, and
(iii) human IgA constant domains, and a human Ig light
chain constant domain, preferably a human Ig kappa
constant domain;
b) a polymeric IgA antibody derived from the IgA antibody
in a);
c) a secretory IgA antibody derived from the polymeric IgA
antibody in b).

In some embodiments, the antibody is coupled to a labeling agent which produces a detectable and/or quantifiable signal, in particular a radioactive, magnetic or luminescent (radioluminescent, chemiluminescent, bioluminescent, fluorescent or phosphorescent) agent. The labeled antibody may be labeled directly or indirectly, via covalent or non-covalent bonds, using standard conjugation techniques that are well-known to those skilled in the art.

In a preferred embodiment, the labeled antibody is linked covalently to a radioactive agent, preferably Technetium-99 ($^{99}$Tc).

Covalent coupling of the labeling agent, for example a radioactive agent, to the antibody may be achieved by incorporating a reactive group in a recombinant or synthetic protein, and then using the group to link the labeling agent covalently, as illustrated in the examples of the present application.

The anti-CEA antibody of the invention can be produced by the conventional techniques known to those skilled in the art. For example, monoclonal antibodies are produced from hybridomas obtained by fusion of B lymphocytes of an animal immunized with CEA antigen, with myelomas, according to the technique of Kohler and Milstein (Nature, 1975, 256, 495-497); the hybridomas are cultured in vitro, in particular in fermenters. Chimeric and/or humanized recombinant antibody and antibody fragments can be prepared from hybridoma cells specific for the antigen by the conventional techniques of recombinant DNA cloning and expression. Human antibody can be obtained from a transgenic mouse possessing human immunoglobulin loci.

Human/mouse chimeric monoclonal IgA antibody are advantageously produced from transgenic mouse HAMIGA™ (EP patent 1 680 449 B1) immunized with recombinant CEA antigen. HAMIGA™ is a humanized transgenic mouse strain expressing human/murine chimeric IgAs. Following immunization of HAMIGA™ mice with CEA antigen, hybridomas are produced using standard techniques, as described above. Preferably, the hybridomas are obtained from the mouse myeloma cell line Sp2/0 cell, which expresses immunoglobulin J chain.

Polymeric antibodies are produced by plasma or myeloma cells expressing the immunoglobulin J chain, such as for example the mouse myeloma cell line Sp2/0 cell.

Secretory antibodies are produced in vitro, as previously described (Rindisbacher et al., JBC, 1995, 270, 14220-14228; Koteswara et al., PNAS, 1997, 94, 6364-6368).

The invention relates also to an isolated polynucleotide encoding the antibody of the invention in expressible form. The polynucleotide encoding the antibody in expressible form refers to a nucleic acid molecule which, upon expression in a cell or a cell-free system, results in a functional antibody. The polynucleotide, either synthetic or recombinant, may be DNA, RNA or combination thereof, either single- and/or double-stranded. The polynucleotide is operably linked to at least one transcriptional regulatory sequence and, optionally to at least one translational regulatory sequence. In some embodiments, said polynucleotide encodes the VH and/or VL domain of the monoclonal antibody 15B3 or 14G8.

Preferably, the polynucleotide comprises at least one the following nucleotide sequences:

```
SEQ ID NO: 15:
gacattcagatgacccagtctcctgcctcccagtctgcatctctggga gaaagtgtcaccatcacatgcctggcaagtcagaccattggtacacgg ttagcatggtatcagcagaaaccagggaaatctcctcagctcctgatt tatgcagcaaccaggttggcagatggggtcccatcaaggttcagtggt agtggatctggcacaaaattttattcaagatcagcagcctacaggctg aagattttgtaagttattactgtcaacaactttacagtactccgtaca cgttcggaggggggaccaagctggaaataaaa,
corresponding to the nucleotide sequence of the
V and J genes encoding monoclonal antibody 15B3
light-chain variable domain (VL);

SEQ ID NO: 16:
cagatccagttggtgcagtctggacctgagctgaagaagcctggagag acagtcaagatctcctgcaaggcttctgggtataccttcacaaactat ggaatgaactgggtaaaccaggctccaggaaagggtttaaagtggatg ggctggataaacaccaacactggagagccaacatatgctgaagagttc aagggacggtttgccttctattggaaacctctgccagcactgcctatt tgcagatcaacaacctcaaaaatgaggacacggctacatatttctgtg caagattgtggtacctgtacttcgatgtctggggcgcagggaccacgg tcaccgtctcctca,
corresponding to the nucleotide sequence of the
V, D and J genes encoding monoclonal antibody
15B3 heavy-chain variable domain (VH);

SEQ ID NO: 17:
gatattgtgctaactcagtctccagccaccctgtctgtgactccagga gatagcgtcagtattcctgcagggccagccaaagttttagcaacaacc tacactggtatcaacaaaaatcacatgagtctccaaggcttctcatca agtatgcttcccagtccatctctgggatcccctccaagttcactggca
```

```
-continued
gtggatcagggacagatttcactctcagtatcaacagtgtggagactg aagattttggaatgtatttctgtcaacagagtaacagctggcctctca cgttcggtgctgggaccaagctggagttgaaac,
corresponding to the nucleotide sequence of the
V and J genes encoding monoclonal antibody 14G8
light-chain variable domain (VL);
and SEQ ID NO: 18:
cagatccagttggtgcagtctggacctgagctgaagaagcctggagag acagtcaagatctcctgcaaggcttctgggtataccttcacaaactat ggaatgaactgggtaaaccaggctccaggaaagggtttaaagtggatg ggctggataaacaccaacactggagagccaacatatgctgaagagttc aagggacggtttgccttctattggaaacctctgccagcactgcctatt tgcagatcaacaacctcaaaaatgaggacacggctacatatttctgtg caagattgtggtacctgtacttcgatgtctggggcgcagggaccacgg tcaccgtctcctca,
corresponding to the nucleotide sequence of the
V, D and J genes encoding monoclonal antibody
14G8 heavy-chain variable domain (VH).
```

Another aspect of the invention is a recombinant vector comprising said polynucleotide. The recombinant vector is advantageously an expression vector capable of expressing said polynucleotide when transfected or transformed into a host cell such as a mammalian, bacterial or fungal cell. Recombinant vectors include usual vectors such as for example plasmids and viral vectors.

A further aspect of the invention provides a host cell transformed with said polynucleotide or recombinant vector.

The polynucleotide, vector, cell of the invention are useful for the production of the protein of the invention using well-known recombinant DNA techniques.

The polynucleotide according to the invention is prepared by the conventional methods known in the art. For example, it is produced by amplification of a nucleic sequence by PCR or RT-PCR, by screening genomic DNA libraries by hybridization with a homologous probe, or else by total or partial chemical synthesis. The recombinant vectors are constructed and introduced into host cells by the conventional recombinant DNA and genetic engineering techniques, which are known in the art.

The antibody according to the invention is used to target tumor cells overexpressing CEA for diagnostic and therapeutic purposes.

In the present invention "tumor or cancer cells overexpressing CEA" refers to tumor or cancer cells exhibiting a level of expression of CEA which is significantly higher compared to that of normal cells of the corresponding tissue or organ in a healthy individual. CEA expression level is measured by standard gene expression assays based on quantitative analysis of mRNA (RT-PCR and others) or protein (immunoassay such as ELISA and others).

The invention relates also to a pharmaceutical composition comprising at least an antibody according to the invention and a pharmaceutically acceptable vehicle.

In some embodiments, the antibody is labeled with a radioactive agent suitable for cancer therapy such as with no limitations: Yttrium90, Lutetium177 and Bismuth213.

In some embodiments, the antibody is a polymeric or secretory antibody, preferably an IgA.

The pharmaceutical vehicles are those appropriate to the planned route of administration, which are well known in the art.

The composition of the invention comprises a therapeutically effective dose of antibody, sufficient to inhibit tumor cell proliferation and produce an antitumor effect in the individual having tumor(s) overexpressing CEA to whom it is administered.

The effect of the composition according to the invention can be readily verified by various assays, which are known to the person of ordinary skill in the art such as those described in the examples of the present Application.

The effective dose is determined and adjusted depending on factors such as the composition used, the route of administration, the physical characteristics of the individual under consideration such as sex, age and weight, concurrent medication, and other factors, that those skilled in the medical arts will recognize.

In some embodiments, the composition further comprises at least an anticancer and/or immunomodulatory agent. The anticancer agent may be a chemotherapeutic agent such as for example: Irinotecan, Oxaliplatin, Folinic acid (Leucovorin), Fluorouracil (5FU), Floxuridine (5-fluorodeoxyuridine), Gemcitabine, Folfox (Folinic acid plus 5-FU), Folfiri (Folinic acid plus 5-FU and Irinotecan) and Xelox (Capecitabine plus Oxaliplatin). The anticancer agent may also be another antibody such as an anti-VEGF-receptor antibody. The immunomodulatory agent may be an anti-PD1 or anti-PDL1 agent, in particular an anti-PD1 or anti-PDL1 antibody; a cytokine, for example IL2 or engineered IL-2 variant (IL-2v) with abolished IL-2Rα (CD25) binding, or others. The anticancer or and/or immunomodulatory agent may be advantageously linked to the antibody according to the invention by standard means that are known in the art such as by covalent coupling or making of a genetic fusion.

The invention provides also an antibody or pharmaceutical composition according to the invention for use as a medicament, in particular as anticancer medicament.

The invention provides also an antibody or pharmaceutical composition according to the invention for use in the treatment of a cancer overexpressing CEA.

The invention provides also a method for treating a cancer overexpressing CEA, comprising: administering to an individual a therapeutically effective amount of the composition as described above.

The composition of the present invention is generally administered according to known procedures, at dosages and for periods of time effective to induce anti-tumor effect in the individual. The administration may be by injection or by oral, sublingual, intranasal, rectal or vaginal administration, inhalation, or transdermal application. The injection may be subcutaneous, intramuscular, intravenous, intraperitoneal, intradermal or else.

A secretory antibody, preferably an IgA, is advantageously for oral or local administration (rectal, vaginal, intravesical) or inhalation. A secretory antibody is advantageously used to target the initial tumor.

A polymeric antibody, preferably an IgA, is advantageously administered by injection. A polymeric antibody is advantageously used to prevent metastasis formation and cancer recurrence.

The antibody of the invention is advantageously used in combination with surgery, radiotherapy, chemotherapy, and/or immunotherapy with immunomodulatory agents.

In some embodiments, the antibody of the invention is used for the treatment of humans.

In some embodiments, said cancer is a mucosal epithelium cancer such as gastrointestinal, respiratory and genitourinary, and breast cancers. Non-limitative examples of such cancers include colorectal, gastric, thyroid, lung, breast, pancreas, gallbladder, urinary bladder, ovary and endometrium cancers. Preferably, said cancer is colorectal carcinoma.

A subject of the present invention is also the use of antibody according to the invention, in vitro, for diagnosing a cancer overexpressing CEA.

Another subject of the present invention is the antibody for use, in vivo, for diagnosing a cancer overexpressing CEA.

For diagnostic applications, the antibody, preferably a labeled antibody, is used to detect CEA expression. For example, CEA over-expression may be detected, in situ, in a tissue from a patient, in comparison to the same type of tissue from a healthy individual.

Another subject of the present invention is a kit for diagnosing cancer overexpressing CEA, comprising at least an antibody according to the invention, preferably a labeled antibody, and optionally instructions for the use of the antibody.

A subject of the present invention is also the use of the antibody according to the invention, as a research tool for studying CEA.

Another subject of the present invention is a method for detecting CEA, in vitro and/or in vivo, comprising at least the steps of:
  bringing cells to be analyzed into contact with the labeled antibody, and
  detecting the labeled cells.

The labeled cells are detected by standard techniques known to those skilled in the art.

The detection of CEA, in vivo, in the body of a mammal, comprises a prior step of administering said peptide to said mammal (parenteral injection, oral administration).

The invention encompasses the use of mixtures or combinations of antibodies such as mixtures of different anti-CEA antibodies according to the invention or mixtures of antibodies according to the invention and other antibodies. Non-limitative examples of such mixtures include mixtures of IgA and IgG antibodies directed to the CEA antigen alone or the CEA antigen and another tumor-associated antigen and mixtures of at least one anti-CEA antibody according to the invention with one or more of anti-CD3, in particular anti-CD3 epsilon chain, anti-VEGF receptor, anti-PD1 and anti-PDL1 antibodies.

The invention encompasses also the multivalent and multispecific antibodies corresponding to the above mixtures or combinations of antibodies.

The practice of the present invention will employ, unless otherwise indicated, conventional techniques which are within the skill of the art. Such techniques are explained fully in the literature.

In addition to the above arrangements, the invention also comprises other arrangements, which will emerge from the description which follows, which refers to exemplary embodiments of the subject of the present invention, with reference to the attached drawings in which:

FIG. 1: Western-Blot analysis of IgA monoclonal antibody anti-CEA (clone #15B3) using anti-human alpha-heavy chain antibody as a probe.

Figure 2:
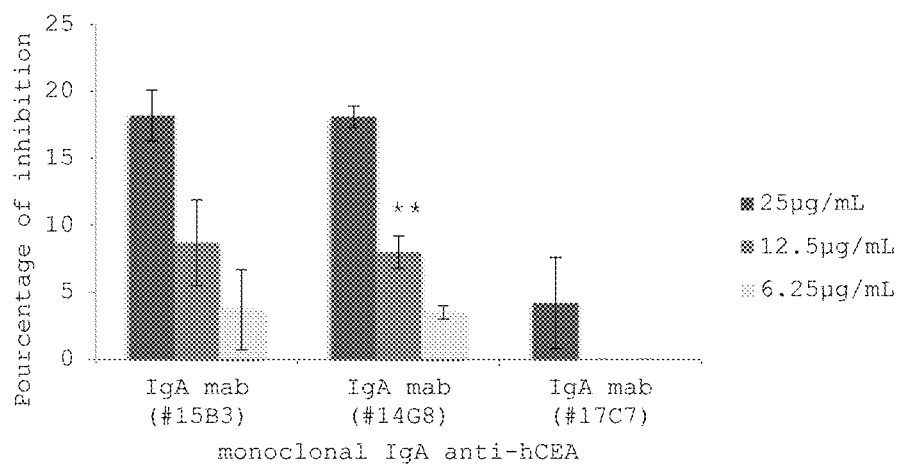
Figure 2:
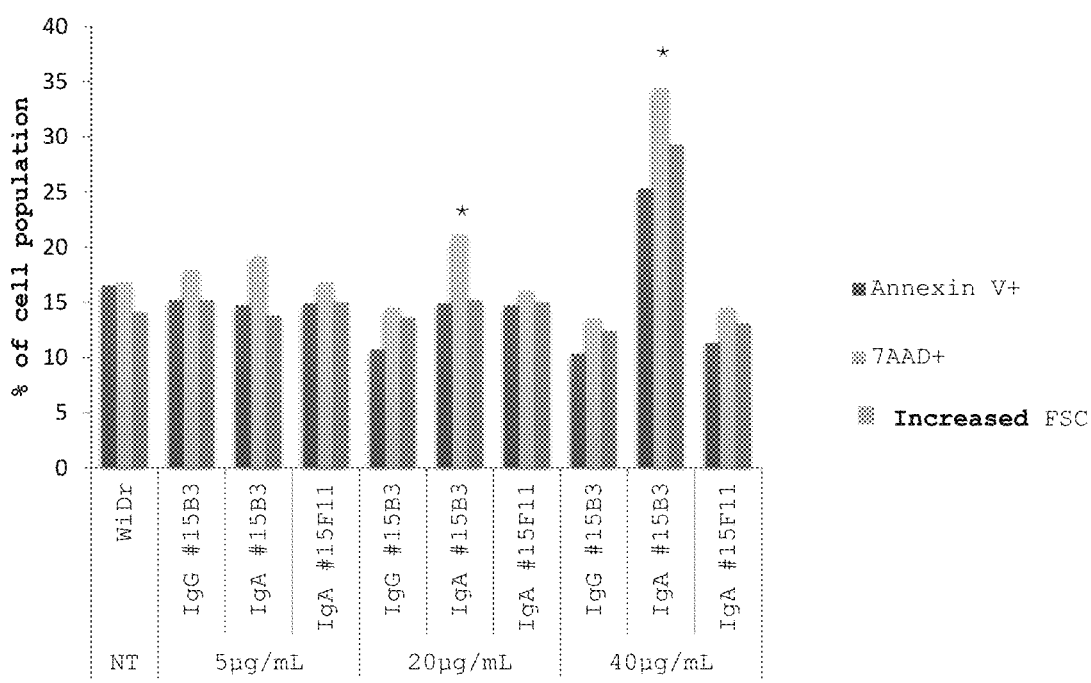

FIG. 2: In vitro direct cancer cell growth inhibition by anti-CEA monoclonal antibody in human colorectal cancer target cells (WiDr– CEA$^+$).
A. Inhibition of cancer cell proliferation by increasing concentrations (6.25, 12.5 and 25 µg/ml) of culture supernatant of IgA anti-CEA positive clones #15B3 and #14G8, compared with a negative clone (#17C7). B. Direct induction of apoptosis in target cells by increasing concentrations (5, 20 and 40 µg/ml) of culture supernatant of IgA anti-CEA clone #15B3, compared with IgG anti-CEA clone #15B3 and irrelevant IgA anti-peanut (IgA #15F11) culture supernatant. *p value≤0.05; **p value≤0.01

Figure 3:
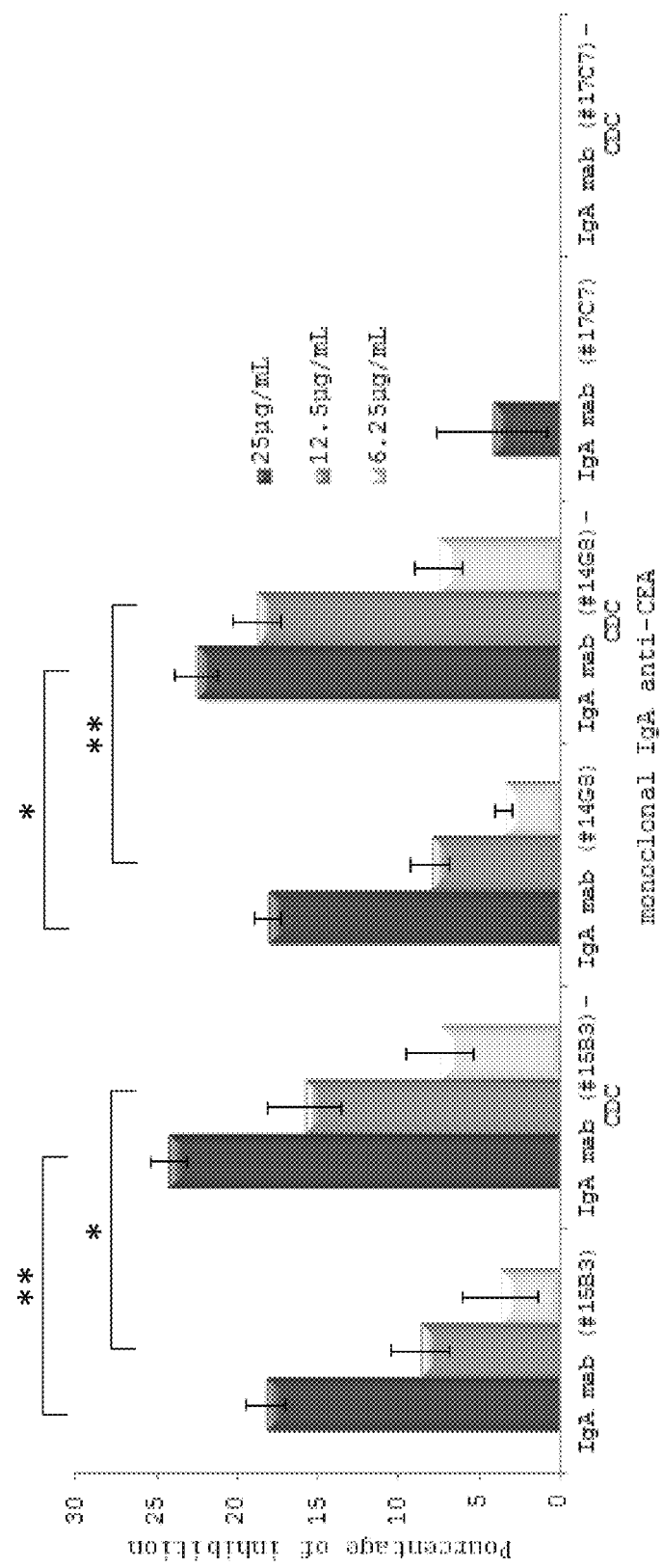

FIG. 3: In vitro complement-dependent cytotoxicity (CDC) induction by IgA monoclonal antibody anti-CEA in human colorectal cancer target cells (WiDr– CEA$^+$).
Inhibition of cell proliferation in target cells was assayed with increasing concentrations (6.25, 12.5 and 25 µg/ml) of culture supernatant of IgA anti-CEA positive clones #15B3 and #14G8 and negative clone #17C7, in the presence (IgA mab(#15B3)-CDC; IgA mab(#14G8)-CDC; IgA mab (#17C7)-CDC) or absence (IgA mab(#15B3); IgA mab (#14G8); IgA mab(#14G8) of complement. *p value≤0.05; **p value≤0.01.

Figure 4:
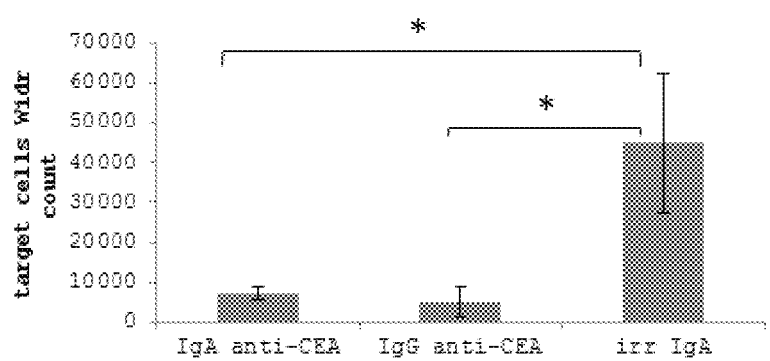
Figure 4:
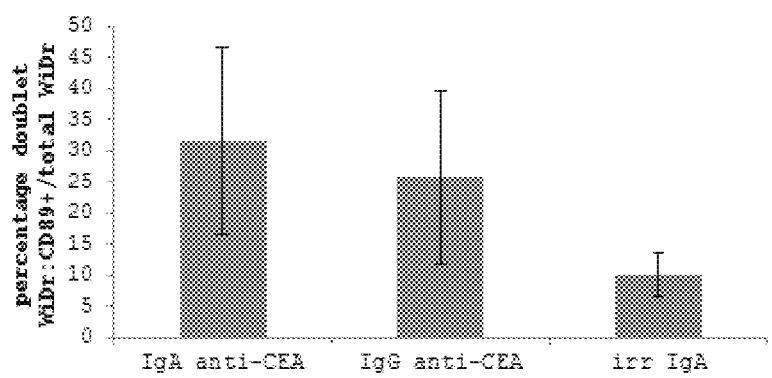

FIG. 4: In vivo ADCC induction by anti-CEA IgA antibody in human colorectal cancer target cells (WiDr– CEA$^+$). Target cells were injected into the peritoneal cavity of transgenic mice expressing human CD89 (Fc-alpha-Receptor) in the presence of purified IgG or purified polymeric IgA anti-CEA or irrelevant IgA anti-peanut (n=4 mice per group). A. Target cell count. B. Percentage of doublet target cells (CEA$^+$)/Effector cells (CD89$^+$) in total target cells. *p value≤0.05.

Figure 5:
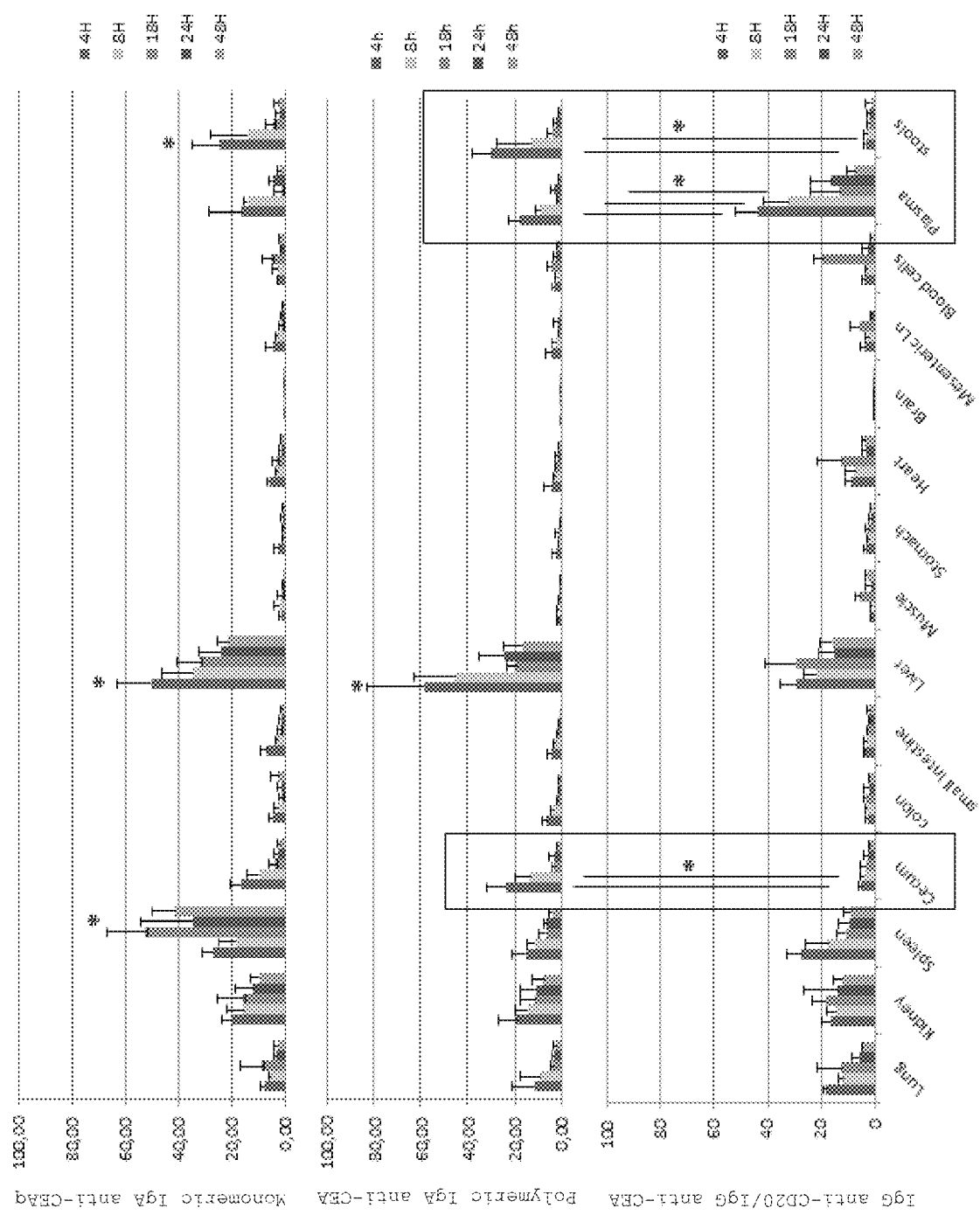

FIG. 5: Biodistribution of $^{99m}$Tc-anti-CEA IgA monomeric-SH, $^{99m}$Tc-anti-CEA IgA polymeric-SH and $^{99m}$Tc-anti-CD20 IgG-SH in healthy Balb/c mice at 4, 8, 18, 24 and 48 h, expressed as the percentage of injected (intravenous; IV) dose per gram, % ID/g (values represent means±SD of the % ID/g). *p value≤0.05.

Figure 6:
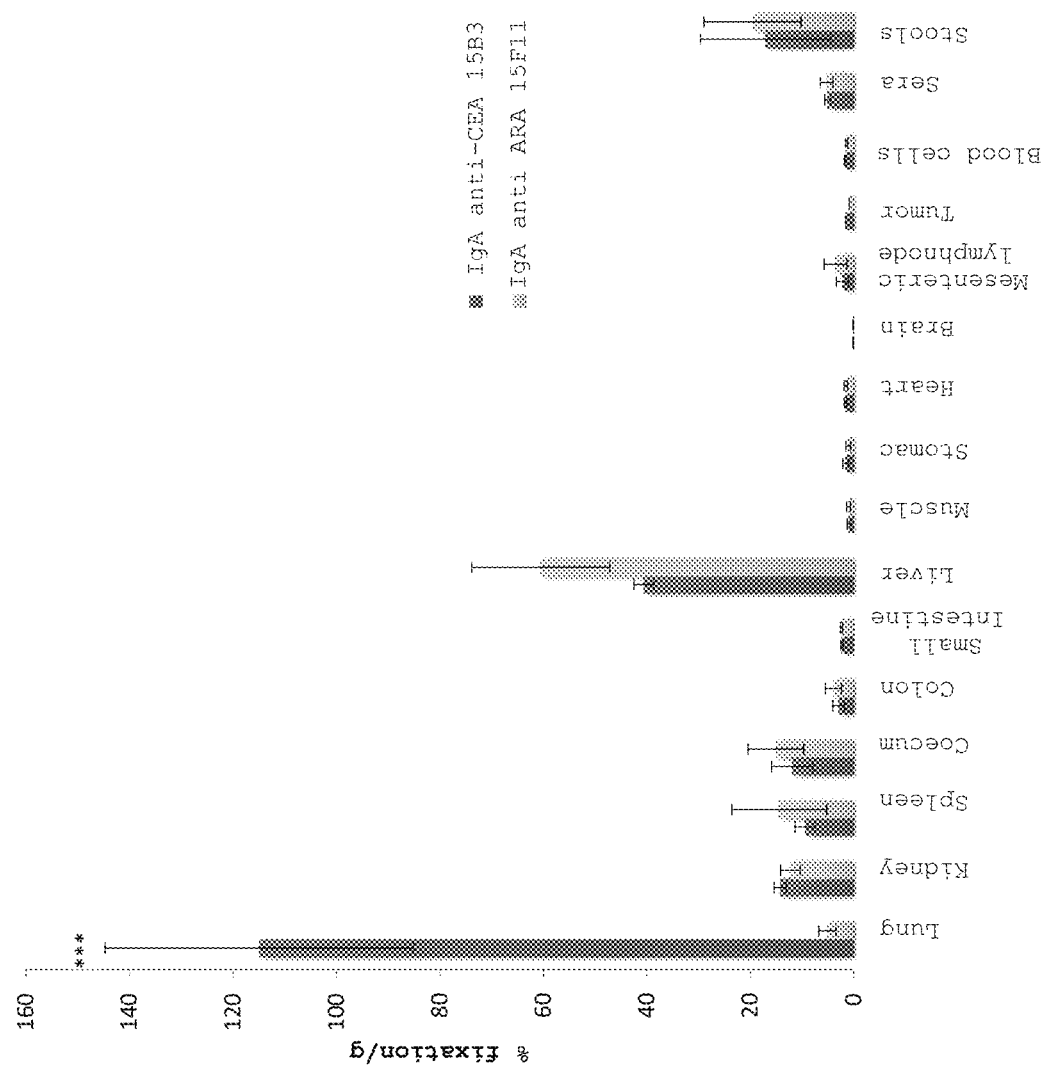

FIG. 6: Biodistribution of $^{99m}$Tc-anti-CEA IgA polymeric-SH and irrelevant $^{99m}$Tc-anti-PEANUT (anti-ARA) in nude mice bearing intracaecal tumours, at 8 h, expressed as the percentage of the injected dose per gram, % ID/g (values represent means±SD of the % ID/g). ***p value≤0.001.

Figure 7:
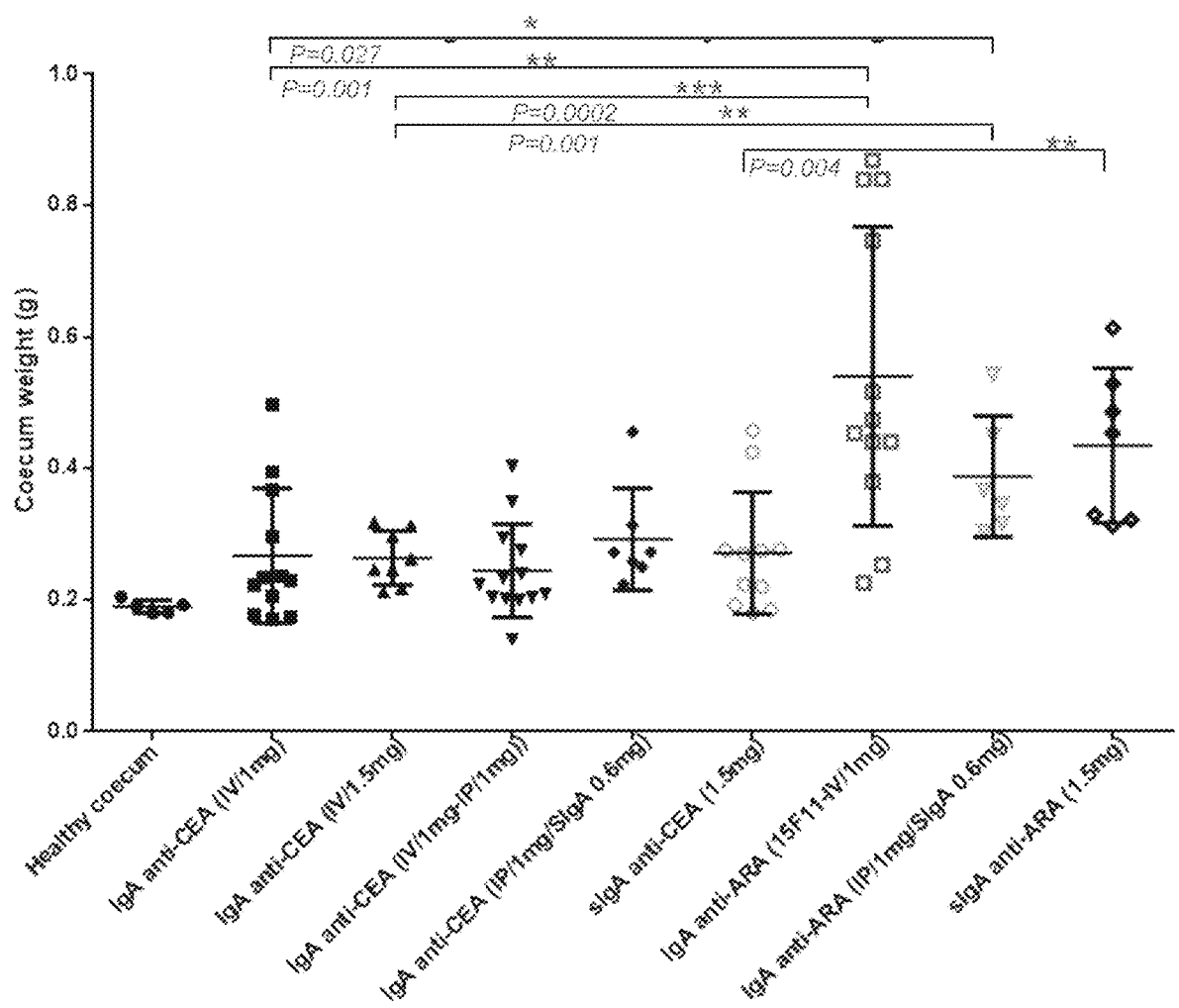

FIG. 7: Colorectal tumor growth inhibition by anti-CEA IgA treatment in orthotopic mouse model of human colorectal cancer. 8 days after tumor cell implantation in nude mice, polymeric IgA anti-CEA (IgA anti-CEA) and irrelevant dimeric IgA anti-peanut (IgA anti-ARA) were administered by the intravenous route (0.2 or 0.3 mg/injection for 5 consecutive days) and IgA anti-CEA (IgA anti-CEA) was also administered by the intravenous (1 mg) and intraperitoneal (1 mg) routes, whereas secretory IgA anti-CEA and irrelevant secretory IgA anti-peanut were administered by the oral route (0.135 mg/day for 11 consecutive days) or oral (0.6 mg) and intraperitoneal (1 mg) routes. 10 weeks after tumor cell implantation, caecum weight of IgA anti-CEA treated mice was compared with that of irrelevant IgA treated controls.

Figure 8:
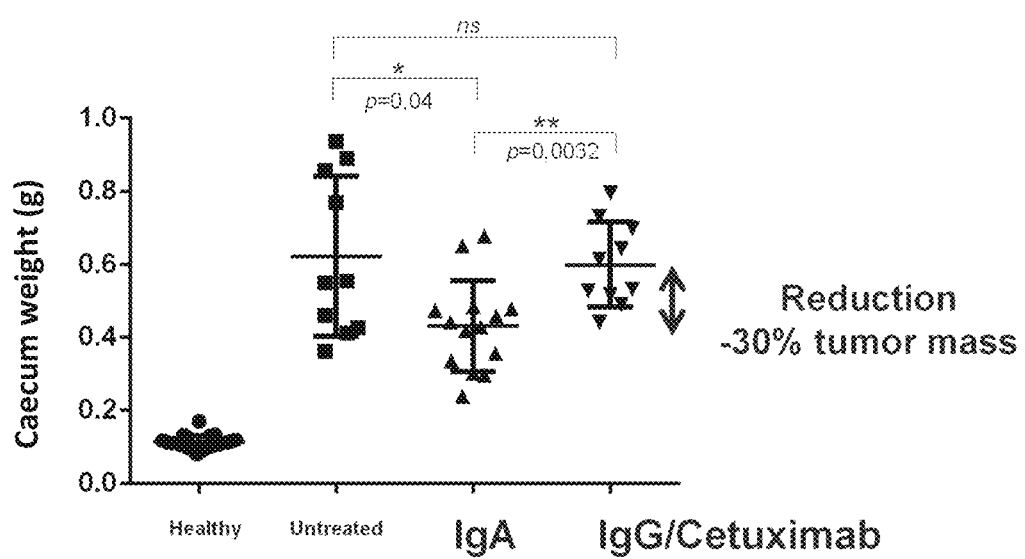

FIG. 8: Colorectal tumor growth inhibition by anti-CEA IgA or anti-EGFR IgG (cetuximab) treatment in orthotopic mouse model of human colorectal cancer. Seven weeks after tumor cell implantation, polymeric IgA anti-CEA (IgA) and anti-EGFR IgG (cetuximab) were administered by the intravenous route (4 mg for each antibody). Ten weeks after tumor cell implantation, caecum weight of IgA anti-CEA and IgG/cetuximab treated mice was compared with that of untreated controls.

EXAMPLE 1: MATERIAL AND METHODS

—Immunization

Immunization was performed in HAMIGA™ transgenic mice (EP Patent 1 680 449 B1), a transgenic mouse strain producing human/mouse chimeric IgAs consisting of human IgA heavy chain constant regions and mouse light chain constant regions and (heavy and light chain) mouse variable regions. HAMIGA™ transgenic mice (4 mice) were immunized by intraperitoneal route twice at two weeks interval with human recombinant CEA (Eurobio-Abcys) or irrelevant antigen (peanut), in Freund adjuvant (10 µg/mouse/injection, ratio 1:1 CFA (SIGMA) and 10 µg/mouse/injection, ratio 1:1 IFA (SIGMA).

—Preparation of Monoclonal IgA

Human chimeric monoclonal IgA (IgA1) against CEA or irrelevant antigen (peanut) were prepared by immortalization of B-cell lymphocytes from CEA-immunized HAMIGA™ mice, according to standard protocol (Kohler, G. & Milstein, C., European Journal of Immunology, 1976, 6, 511-9). Briefly, all splenocytes from CEA-immunized mice were harvested and pelleted before being fused with mice myeloma cells (P3X63 Sp2/0:AG14; ATCC CRL-1581; cellular ration 1 SP2/0 for 3 splenocytes). The hybridomas were subcloned on 96-wells plate. After three weeks of culture, supernatants of hybridoma clones were harvested and tested for their biological activity or antigen affinity. Each clone was cryopreserved in DMSO 10%/SVF 20%/DMEM media in liquid nitrogen.

—Ig cloning and sequencing

Ig cloning and sequencing was performed using standard cloning and sequencing techniques.

—Preparation of Recombinant IgG1

Recombinant human-mouse chimeric IgG1 anti-CEA was synthesised after cloning the mouse variable regions of the heavy and light chains of anti-CEA human-mouse chimeric IgA1. It was then produced in human embryonic kidney cells (HEK 293).

—Ig radiolabelling with $[^{99m}Tc(CO)_3(H_2O)_3]^+$

IgA radiolabelling method was adapted from the radiolabelling method previously described for IgG (Carpenet et al., PLoS One, 2015 Oct. 6; 10(10):e0139835). Briefly, the first step was thiol-derivatisation of Ig with 2-iminothiolane. Next, 0.5 to 2.2 nmol IgA and IgG (300 µL in PBS) were incubated with 2-IT (3.8 µM, 25° C., 120 min). The solutions were purified by size exclusion chromatography. The number of thiol groups was determined by a micromethod using Ellman's reagent (5.5'-dithiobis-2-nitrobenzoic acid, DTNB). The second step was synthesis of the tricarbonyl precursor $[^{99m}Tc(CO)_3(H_2O)_3]^+$. Next, 0.8-1 mL of freshly eluted $[Na^{99m}TcO_4]$ (CisBio, Codolet, France) in fixed activities (2,220-3,700 MBq) was added to the IsoLink® kit (Covidien, Petten, The Netherlands) and incubated for 25 min at 100° C. Radiochemical purity (RCP) analysis was performed by thin-layer chromatography (TLC) using two systems to separate the $[^{99m}Tc(CO)_3(H_2O)_3]^+$ from free $[^{99m}Tc]$-pertechnetate, reduced $^{99m}Tc$ and hydrolysed $[^{99m}Tc(OH)_n(H_2O)_y]$ (Baker-flex aluminium, MeOH/HCl (95/5 v/v); instant thin layer chromatography-silica gel (ITLC-SG), MeOH; JT Baker Inc., Phillipsburg, N.J., USA). The $^{99m}Tc$-Isolink® labelling yields were superior to 98%. The third and last step was the radiolabelling of native or derivatised Ig with $[^{99m}Tc(CO)_3(H_2O)_3]^+$. A total of 0.5-2.2 nmol of non-derivatised IgA or derivatised IgA-SH, or 1.5 nmol IgG-SH in 300 µL of PBS, was incubated for 120 min (25° C.) with 150 µL (148-185 MBq) of a $^{99m}Tc$-tricarbonyl solution, previously neutralised to pH 7.0 (0.5 M HCl). RCP was determined by TLC with ITLC-SG/NaCl 0.9%.

—Ig Purification

The antibodies were purified by affinity chromatography using a Tricorn Column 5/100 with protein A-Sepharose at a flow rate of 1.0 mL/min (GE Healthcare, Waukesha, Wis., USA) and were eluted with glycine (0.1 M pH 2.7) equilibrated in Tris/base (1.0 M). Subsequently, IgA and IgG were dialysed against phosphate-buffered saline (PBS) by centrifugation (1,000×g, 15 min) using Amicon 30 kDa (Millipore, Saint-Quentin, France). The protein concentrations were determined before and after radiolabelling using Micro Bicinchoninic Acid (BCA™) Protein Assay kit (ThermoFisher Scientific, Elancourt, France), using bovine serum albumin (BSA) as a standard with quantification limits of 2.5 and 100 µg/mL.

—Purification of Monomeric and Polymeric IgA

Total IgA were purified using CAPTURESELECT™ IgA Affinity Matrix (ThermoFisher Scientific), according to manufacturer's instructions. Monomeric and polymeric forms of IgA were then separated by size exclusion column chromatography using HILOAD™ 26/600 SUPERDEX™ 200 pg (GE Healthcare), according to manufacturer's instructions. An enriched fraction of the monomeric (mIgA) or polymeric (pIgA) form was obtained (purities of 95% and 85%, respectively).

—Secretory IgA Preparation

Anti-CEA secretory IgA was produced by in vitro covalent bond with recombinant human secretory component (hSC), as previously described (Rindisbacher et al., JBC, 1995, 270, 14220-14228; Koteswara et al., PNAS, 1997, 94, 6364-6368). Briefly, human secretory component cDNA was amplified by PCR from ileum RNA preparation and inserted into mammalian expressing vector (pCDNA.3, Invitrogen). Recombinant hSC was expressed in HEK-293 cells and purified by affinity chromatography. In vitro covalent assembly of hSC and dimeric IgA was performed by incubating hSC and dimeric IgA during 1 h at 37° C. (at a protein mass ration 1:1).

—Antigen Specificity Analysis

CEA specific IgA were assessed by ELISA using Maxisorp® 96-wells plates (NUNC) coated with 1 to 5 µg/mL of antigens overnight at 4° C. Crude supernatants of unpurified IgA (diluted in PBS/Gelatin 0.2%) were incubated 2 hours at 37° C. Specific IgA binding was revealed with an AP-conjugated goat anti-human IgA antibody (1/2000 diluted, Beckman Coulter).

—Purified Monomeric and Polymeric IgA and Secretory IgA Concentration Titration by ELISA Purified IgA (purified by affinity chromatography) and secretory IgA were titered by ELISA. Briefly, 96-well plates (NUNC, Maxisorp®) were coated with 1 µg/mL of goat anti-human IgA (Beckman Coulter) in PBS buffer at 4° C. overnight. Wells were saturated in PBS buffer containing 2% BSA during 30 minutes at 37° C. Incubation of the samples (secretory IgA, diluted 10 times in PBS containing 0.2% BSA; purified IgA, diluted 100 times in PBS containing 0.2% BSA) was performed at 37° C. during 2 h. Human IgA calibrator range (from [control hIgA]=0.2 mg/ml to 1.56 ng/mL) was incubated following the same protocol and revealed by an Alkaline-Phosphatase (AP) labelled goat anti-hIgA polyclonal antibody (Beckman Coulter; diluted 2000 times in PBS containing 0.2% BSA).

—Cell Culture

WiDr, a human colorectal cell line expressing CEA, derived from a primary adenocarcinoma of the rectosigmoid, was purchased from ATCC (VA, USA) (WiDr ATCC® CCL-218™). HT-29, human cell line from colorectal adenocarcinoma was purchased from ATCC (HTB-38™). The cell lines were grown in DMEM or in RPMI, supplemented with 10% fetal calf serum (FCS), 1% sodium pyruvate, 1% (100 U/ml) penicillin-streptomycin (100 µg/ml). Medium was also supplemented with 1% of nonessential amino acids and 1% of glutamine.

—In Vitro Cellular Growth Inhibition

Cells were harvested when reached the log phase growth stage. Cells were then plated at 50,000 cells/well in 1004 and incubated overnight. Culture media was removed and replaced by culture media (DMEM/FCS10%) containing various concentrations of the antibodies (anti-CEA IgA, irrelevant anti-Peanut IgA, recombinant IgG anti-CEA). After 48 h of incubation, ALAMARBLUE™ was added aseptically in an amount equal to 10% of the culture volume. Cultures were replaced to incubator. At various time, fluorescence/absorbance was measured. Absorbance was measured at a wavelength of 600 nm. To evaluate the impact of fresh human complement elements on cellular growth inhibition, culture media was removed and replaced by media (DMEM) containing 10% of fresh human sera with various concentrations of antibodies (anti-CEA IgA, anti-Peanut IgA, recombinant IgG anti-CEA).

—Apoptosis Assay

Apoptosis assay was performed using PE Annexin V Apoptosis Detection kit I, according to manufacturer's instructions (BD PHARMINGEN™). Briefly, cells harvested when reached the log phase growth stage were plated at 50,000 cells/well in 1004 and incubated overnight. Culture media was removed and replaced by culture media (DMEM/SVF10%) containing various concentrations of the antibodies (anti-CEA IgA, irrelevant anti-Peanut IgA, recombinant IgG anti-CEA). After 48 h of incubation, cells were harvested, washed several times in PBS and diluted at $10^6$ cells/mL in Binding Buffer (BD PHARMINGEN™). Cells are incubated with PE-conjugated Annexin V (BD PHARMINGEN™) during 15 minutes at room temperature. Cells were washed in Binding Buffer and resuspended in 1× Binding Buffer. 7AAD Viability Staining Solution (BD PHARMINGEN™) was added just prior analyzing by flow cytometry.

—In Vivo Antibody-Dependent Cellular Cytotoxicity (ADCC)

A transgenic SCID-CD89 mouse model (provided by Pr Jeannette Leusen, Utrecht University, Netherland), in which neutrophils and monocytes express the human CD89 has been used. $10^7$ cells were incubated at $10^6$ cells/mL with polymeric IgA anti-CEA, polymeric IgA anti-Peanut or recombinant IgG anti-CEA (at 20 µg/mL) during 1 h at 4° C. Target cells ($CEA^{positive}$-WiDr adenocarcinoma) were pelleted, resuspended in PBS and injected into the peritoneal cavity. 16 to 18 h post-inoculation, cells were harvested by peritoneal cold washing and cell populations were analyzed by flow cytometry (FACS) using FITC-anti-CD89 antibody (BioLegend) staining. Effector cells were identified by selective expression of $CD89^{positive}$ on cell surface and cancer cells were gated by their characteristics of cellular size and structure.

—Orthotopic Mouse Model of Human Colorectal Cancer (CRC)

All in vivo experiments were performed in accordance with animal ethical regulations and all efforts were made to minimize suffering. Direct orthotopic cell microinjection (OCMI) was performed according to Cespedes method (Cespedes et al., Am. J. Pathol., 2007, 170, 1077-1085). Briefly, seven-week-old female nude mice (athymic nude, HARLAN Laboratories) or transgenic SCID-CD89 mice (provided by Pr Jeannette Leusen, Utrecht University, Netherland) were anesthetized with ketamine (80 mg/kg; Imalgene (100 mg/ml), MERIAL) and xylazine (9.6 µg/kg; 2% Rompun, BAYER) to exteriorize their caecum by a laparotomy. WiDr cells ($2.10^5$ cells suspended in 10 µl of PBS in a sterile micropipette) were slowly injected between the mucosa and the muscularis externa layers of the caecum wall, under a binocular lens, with an approximate 30° angle. After injection, the caecum was returned to the abdominal cavity. Animals were treated by veterinary antibiotics to prevent intraperitoneal infection. Peritoneal cavity was closed by surgical laparotomy. If animals demonstrated clinical alteration or weight loss, animals were euthanized by anesthesia and cervical dislocation.

—Biodistribution of $^{99m}$Tc-Anti-CEA IgA-SH and $^{99m}$Tc-Anti-CEA IgG-SH in Normal Mice and Human CRC Mouse Model Biodistribution experiments were carried out in 7-week-old male BALB/c mice (Charles River Laboratories, chalaronne, the L'ARBRESLE Cedex) or xenografted nude mice. $^{99m}$Tc-IgA-SH monomeric or $^{99m}$Tc-IgA-SH polymeric or 99mTc-IgG-SH (40 MBq, 170 µg of antibody) was injected intravenously (tail vein) to BALB/c mice. 6 to 8 weeks after OCMI procedure, xenografted nude mice were divided into 2 groups. The first group (n=6) received intravenously 170 µg $^{99m}$Tc-anti-CEA pIgA-SH and the second (n=6) 170 µg of $^{99m}$Tc-anti-PEANUT pIgA-SH (All mice received an activity of 35-37 MBq). Nude mouse controls received the same $^{99m}$Tc-anti-CEA pIgA-SH. Animals were euthanized by anesthesia and cervical dislocation, at different times after administration (4 h, 8 h, 18 h, 24 h, 48 h post-injection for BALB/c mice; 4 h and 8 h for xenografted nude mice). Selected tissues were excised, rinsed, and weighed, and their radioactivity levels were measured with a gamma-counter. The uptake of radioactivity in these organs was expressed as a percentage of the injected dose per gram of tissue (% ID/g) after correcting for radioactive decay for each time point. Blood cells, plasma, and feces were also collected and measured. Faeces refers to faecal matter collected in the small intestine and colon during dissection. Furthermore, the caecum was longitudinally opened washed with PBS and countered separately from caecal feces to evaluate luminescent IgA. The caecum and lungs of xenografted nude mice were fixed with buffered formalin during radioactive decay (48 h).

—Histological Analysis of Human Colorectal Orthotopic Grafts

Mice organs were transferred to 4% formalin and include in paraffin after an automated cycling of dehydration system. 4 µm sections were prepared using microtome. For histological analysis, slides were stained with hematoxylin eosin and saffron (HES analysis), with alcian blue (secreting mucus analysis). For vascularization analysis, CD31 staining was made using VENTANA robot.

—In Vivo Inhibition of Tumor Growth

Experiments were performed in the orthotopic mouse model of human colorectal cancer (CRC) described above. The IgA anti-CEA antibody and the irrelevant IgA anti-peanut antibody were administered 8 days after implantation of human tumor cells in the caecum of Balb/c Nude mice (n=12 per group). Two routes of administration have been evaluated: the intravenous (by administration of 0.2 or 0.3 mg/injection for 5 consecutive days) for the polymeric IgA and the oral (by administration of 0.135 mg/day for 11 consecutive days) for the secretory IgA. 8 weeks after the end of the treatment, animals were euthanized by anesthesia and cervical dislocation and the caecum were excised, emptied, rinsed and weighed.

EXAMPLE 2: IDENTIFICATION OF ANTI-CEA MONOCLONAL ANTIBODIES HAVING DIRECT GROWTH-INHIBITORY ACTIVITY ON CEA EXPRESSING TUMOR CELLS

IgA monoclonal antibodies (Mabs) anti-CEA were generated by immunization of HAMIGA™ transgenic mice, a transgenic mouse line producing human/mouse chimeric antibodies having human IgA heavy chain constant regions and mouse light chain constant regions and (heavy and light chain) mouse variable regions. Hybridomas were produced after fusion of B cells of the immunized HAMIGA™ mice with the Sp2/0 mouse myeloma cell line. As the Sp2/0 line is derived from murine myeloma expressing murine J chain necessary for the dimerization of the IgA, the hybridomas which were obtained produce distinct forms of IgA MAbs anti-CEA: a monomeric form (without J chain) and a polymeric form which contain J chain(s) and includes dimeric form and higher polymeric forms of IgA (FIG. 1). The level of expression of the various forms of IgA depends on the selected hybridoma. The different forms can be purified and separated by chromatography.

Hybridoma clones were selected for direct cancer cell growth-inhibitory activity on various CEA expressing human tumor cell lines using ALAMARBLUE™ assay.

Anti-CEA IgA of clone 15B3 (also named #15B3) and clone 14G8 also named #14G8) block cell growth of two cell lines derived from human colorectal adenocarcinoma (WiDr, 18.2%±1.9% for 15B3 and 18.1±1.2 for 14G8 at 25 µg/mL (culture supernatant); FIG. 2). These positive clones were selected for further analysis. Variable regions from IgA heavy and light chains (VH and VL) were cloned and sequenced. The VL and VH amino acid sequences correspond to SEQ ID NO: 11 and 12 and SEQ ID NO: 13 and 14, respectively for 15B3 and 14G8. The nucleotide sequences encoding said amino acid sequences correspond to SEQ ID NO: 15 and 16 and SEQ ID NO: 17 and 18, respectively for 15B3 and 14G8.

A recombinant anti-CEA IgG1 derived from clone 15B3 was constructed using the cloned VH and VL domains and expressed in Sp2/0 or HEK cell line. RecIgG1 anti-CEA #15B3 shows a counterpart level of growth inhibition in comparison to IgA anti-CEA (clone #15B3). The affinity of the antibody (mainly carried by the variable regions forming the "paratope") is preserved during the process of transformation of an IgA1 towards an IgG1.

Increasing doses of anti-CEA IgA (5, 20 and 40 µg/mL, clone #15B3) induces early mechanisms of apoptosis (fixation of Annexin V, permeabilization of the membrane visualized by labelling by 7AAD+(FIG. 2B, significantly higher than for other conditions (recIgG recombinant #15B3, irrelevant IgA1 (anti-peanut #15F11)). The higher valence of a polymeric IgA would allow a potential cross-linking of CEA on the surface of target cells WiDr, inducing an unexpected biological effect (direct apoptosis) stronger and faster than a monomeric form of IgA, as in the case of recIgG1 #15B3.

IgA recruits elements of the complement leading to lysis of the cell target via the alternate pathway. Same tests of cell growth inhibition of WiDr cancer cells were performed in the presence of human sera (human sera alone did not affect biologically WiDr cell culture). A significant rise of growth inhibition was recorded in the presence of human complement for the two selected anti-CEA IgA clones (clone #15B3 and clone #14G8; FIG. 3).

In humans, IgA recruits also immune effector cells that express a high affinity IgA receptor (Fc-alphaR or CD89), mainly neutrophils and monocytes, two particularly numerous cells in blood cell population. To demonstrate the ability of effector cells recruitment mediated by the anti-CEA IgA #15B3, a transgenic mouse model in which neutrophils and monocytes express the human CD89 has been used. Flow cytometry (FACS) analysis shows the presence of a new population of doubly selected cells (Effector Cell (CD89$^+$): WiDr target cells (CEA$^+$) in mice treated with the anti-CEA IgA (31%±15%) compared with mice treated with irrelevant IgA (anti-peanut IgA; 10.2%±3.5%, FIG. 4). These results demonstrate that the anti-CEA IgA recognizes in vivo CEA on the surface of WiDr cancer cells and induces the recruitment of cells (monocytes/macrophages and polynuclear cells) via the CD89 receptor. In the presence of anti-CEA IgA (#15B3), a very powerful cytotoxic effect eliminates more than 80% of the cancer cell population in 16 h to 18 h (FIG. 4). Compared to the WiDr population harvested in mice treated with the irrelevant IgA, only 16.4%±3.6% of WiDr target cells are harvested after treatment with the specific anti-CEA IgA (#15B3).

Cell types recruited preferentially by IgG and IgA are different: it is known that the IgG-mediated ADCC is induced by the NK cells, strongly expressing the FcgammaR. The recombinant IgG generated from the variable regions of the IgA anti-CEA clone (#15B3) induces a cytotoxic cell lysis of WiDr-CEA$^+$ as strong as the "original" IgA as only 11.3%±8.6% of WiDr were harvested by peritoneal washing after treatment with recIgG anti-CEA (FIG. 4).

The similar cytotoxic effect of the two antibodies supports the demonstration that the IgA is able to induce the ADCC mechanisms as quickly and effectively as the IgG. It also validates that the transformation of the IgA towards IgG does dot modify the affinity of the antibody for its target.

In addition, immunofluorescence analysis on tissues (liver and stomach, data not shown) and flow cytometry analysis on leukocytes (data not shown) demonstrated that the anti-CEA antibody #15B3 does not cross-react with CEACAM-6 (NCA or CD66c).

In conclusion, the anti-CEA antibodies according to the invention have a direct cell growth inhibition effect on cancer cells expressing CEA. This unique antitumor effect is further enhanced by their ability to recruit the complement pathway and the immune cell-effectors of antibody dependent cell cytotoxicity (ADCC) leading to cancer cell lysis. All these antitumor effects are specific for the targeted tumor cells because the antibodies are specific for CEA.

EXAMPLE 3: BIODISTRIBUTION OF ANTI-CEA ANTIBODY IN NORMAL MICE AND ORTHOTOPIC MOUSE MODEL OF HUMAN COLORECTAL CARCINOMA

Bio-distribution and pharmaco-kinetic studies were performed using different forms of Ig, IgA (monomeric (mIgA) and polymeric (pIgA)) and IgG, all labelled with technetium 99m ($^{99m}$Tc). Very quickly, from 8 h post-injection (by i.v.) to normal Balb/c mice, monomeric IgA concentration dropped in sera and it's even more marked for the polymeric IgA to the detectable limit (FIG. 5). Conversely, the concentration of the polymeric IgA (and monomer, to a lesser extent) is quantifiable as early as 4 h post-iv injection, in the caecum, the lung and the liver (FIG. 5). Hepatic-biliary cycle of the IgA is particularly patent here, the circulating IgA is quickly captured by the liver, directed to the gallbladder to be excreted with bile into the lumen of the digestive tract. This is what explains the strong labelling of the liver on the one hand and of the intestinal fluid and stools on the other hand. As early as 4 h post-injection, the secretory IgA is detectable in the lumen of the mucosal organs. In this healthy murine model, the polymeric IgA tropism for the caecum is the strongest and the fastest, superior to the tropism of the monomeric IgA, but also that of the IgG, already described to persist longer in blood.

In conclusion, bio-distribution studies of $^{99m}$Tc-anti-CEA IgA monomeric-SH and $^{99m}$Tc-anti-CEA IgA polymeric-SH in normal Balb/c mice confirmed rapid and strong mucosal tropism of pIgA and, to a lesser extent, mIgA.

To evaluate IgA targeting potency, a CRC tumour model was created in which human cancer cells were grafted in the mucosal environment. Pathological microscopic analysis clearly revealed a structural glandular architecture of the grafted tumour and the presence of large vacuoles in the WiDr cell line, consistent with muco-secretions in the lamina propria layer. Cancer cells invaded the normal caecum, under the muscle layer through the lamina propria, to produce protruding polyps in the lumen. Depending on the delay after direct orthopic microinjection, different stages of CRC have been observed from localised tumours to metastasis in the lungs. Immunohistochemical analysis in tumours revealed that tumour cells were present within tumour vessels, suggesting cellular dissemination by the vascular system. All of these factors led to consider colorectal orthotopic grafts as being useful models of human CRC, because they share the same characteristics as human tumours.

After 8 weeks, tumor cells were spread and identified by immunohistochemistry, as pulmonary metastases (no trace of hepatic colonization is detected in this model). Invasion of the lung capillaries and the presence of cancerous nodules in the lung tissue were particularly identifiable by HES staining. $^{99m}$Tc-anti-CEA IgA polymeric-SH or irrelevant $^{99m}$Tc-anti-PEANUT pIgA-SH were then administered intravenously. Very quickly (already at 4 h postinjection), the radioactive tracer is detected in the lung (FIG. 6). The anti-CEA IgA is able to recognize tumor cells very quickly and with a very strong affinity while metastases are small (observable only on immunohistochemistry slides, no macroscopic tumor is visible). The administration of an irrelevant IgA labelled with $^{99m}$Tc failed to detect any metastasis foci when administered to animals with lung metastases at the same stage of development as animals treated with the specific anti-CEA IgA. These studies confirm the fast mucosal tropism of the IgA antibody (8 h post-injection) and strong targeting power of early metastatic foci in vivo (in the lung).

EXAMPLE 4: ANTITUMOR EFFECT OF ANTI-CEA ANTIBODY IN ORTHOTOPIC MOUSE MODEL OF HUMAN COLORECTAL CARCINOMA

The antitumor effect of the anti-CEA antibody (#15B3) was evaluated in the orthotopic mouse model of human colorectal carcinoma disclosed in example 1. Preliminary results showed a significant benefit of treatment with the polymeric form of anti-CEA IgA on the survival of the animals and the decrease in tumor growth.

In a first experiment, the treatment was administered 8 days after the implantation of human tumor cells in the caecum of mouse (Balb/c Nude, Harlan) for all conditions. Two routes of administration have been evaluated: the intravenous (by administration of a dose/day for 5 days, 8 days after implantation of the tumor) for the polymeric IgA and the oral (by administration of a dose/day for 11 days, 8 days after tumor implantation) for the secretory IgA. When animals (n=12) are treated with a cumulative dose of 1 mg (IV, 0.2 mg/injection for 5 consecutive days), the reduction of the tumor mass is significant compared with the group treated with a cumulative dose of 1 mg (IV, 0.2 mg/injection for 5 consecutive days) of irrelevant polymeric anti-peanut IgA (, p=0.001). The combination of intravenous administration of 1 mg and intraperitoneal administration of 1 mg of polymeric anti-CEA IgA prevents tumor growth as effectively as an only intravenous administration of 1 mg of anti-CEA IgA (FIG. 7). The reduced tumor mass is even more marked by intravenous administration a higher cumulative dose (1.5 mg) of polymeric anti-CEA IgA (0.3 mg/injection 5 days; *, p=0.0002) compared to the group treated with an irrelevant polymeric anti-peanut IgA (FIG. 7). Secretory IgA is the unique isotype able to be administered orally without undergoing enzymatic degradation tumor growth was significantly reduced by oral administration of 1.5 mg of anti-CEA secretory IgA (0.135 mg/administration 11 days, 8 days after implantation) compared to oral administration of an irrelevant secretory IgA (sIgA anti-peanut) (FIG. 6; **, p=0.004).

In a second experiment, seven weeks after the implantation of human tumor cells in the caecum of mouse (transgenic SCID-CD89), polymeric IgA anti-CEA (4 mg) or IgG anti-EGFR (cetuximab; 4 mg) was administered intravenously to engrafted mice (n=10 per group).

The cecal tumor mass was significantly reduced (by about 30%) in anti-CEA IgA treated mice compared to cetuximab treated-mice (FIG. 8; **, p=0.0032).

These results show the effectiveness of the anti-CEA IgA antibodies according to the invention in preventing growth of the primary tumor located in the intestinal mucosal environment. The Anti-CEA IgA demonstrates for the first time a greater therapeutic benefit than the Gold standard treatment for advanced colorectal cancer immunotherapy, the cetuximab-ERBITUX®/anti-EGFr IgG. In addition, high lung uptake of $^{99m}$Tc-anti-CEA pIgA-SH in the mouse tumour model (example 3) suggested efficient targeting potency of pIgA. Due to intrinsic mucosal tropism and biomarker affinity, polymeric IgA could reach its targets very effectively. This work clearly demonstrated the potential of the anti-CEA IgA antibodies according to the invention for the diagnosis and treatment of mucosal tumors.

The invention claimed is:

1. An antibody against carcinoembryonic antigen (CEA) which has a direct tumor cell growth inhibition activity on tumor cells expressing CEA and which comprises light-chain (VL) and heavy-chain (VH) variable domains complementarity-determining region (CDR) sequences selected from the group consisting of:
   (a) the VL-CDR1 sequence of SEQ ID NO: 1; the VL-CDR2 sequence AAT; the VL-CDR3 sequence of SEQ ID NO: 2; the VH-CDR1 sequence of SEQ ID NO: 3; the VH-CDR2 sequence of SEQ ID NO: 4; the VH-CDR3 sequence of SEQ ID NO: 5; and
   (b) the VL-CDR1 sequence of SEQ ID NO: 6; the VL-CDR2 sequence YAS; the VL-CDR3 sequence of SEQ ID NO: 7; the VH-CDR1 sequence of SEQ ID NO: 8; the VH-CDR2 sequence of SEQ ID NO: 9; the VH-CDR3 sequence SEQ ID NO: 10.

2. The antibody according to claim 1, which has a variable region formed by the association of a VL domain of SEQ ID NO: 11 and a VH domain of SEQ ID NO: 12 or a VL domain of SEQ ID NO: 13 and a VH domain of SEQ ID NO: 14.

3. The antibody according to claim 1, which is a human/mouse chimeric antibody.

4. The antibody according to claim 1, which is an IgA.

5. The antibody according to claim 1, which is a polymeric antibody.

6. The antibody according to claim 1, which is a secretory antibody.

7. The antibody according to claim 1, which is a polymeric or secretory IgA antibody.

8. The antibody according to claim 1, which is coupled to a labeling agent.

9. A pharmaceutical composition comprising at least an antibody according to claim 1 and a pharmaceutically acceptable vehicle.

10. A method of treating cancer overexpressing CEA, comprising administering to an individual a therapeutically effective amount of the antibody according to claim 1.

11. An in vitro method of diagnostic of cancer overexpressing CEA, comprising detecting CEA expression in a tissue sample from an individual using the antibody according to claim 1.

12. The method according to claim 10, wherein said cancer is a mucosal epithelium cancer.

13. The method according to claim 10, wherein said cancer is selected from the group consisting of: colorectal, gastric, thyroid, lung, breast, pancreas, gallbladder, urinary bladder, ovary and endometrium cancers.

14. The method according to claim 11, wherein said cancer is a mucosal epithelium cancer.

15. The method according to claim 11, wherein said cancer is selected from the group consisting of: colorectal, gastric, thyroid, lung, breast, pancreas, gallbladder, urinary bladder, ovary and endometrium cancers.

\* \* \* \* \*

SEQUENCE LISTING

```
<160> NUMBER OF SEQ ID NOS: 18

<210> SEQ ID NO 1
<211> LENGTH: 6
<212> TYPE: PRT
<213> ORGANISM: artificial sequence
<220> FEATURE:
<223> OTHER INFORMATION: synthetic peptide

<400> SEQUENCE: 1
```

```
Gln Thr Ile Gly Thr Arg
1               5

<210> SEQ ID NO 2
<211> LENGTH: 9
<212> TYPE: PRT
<213> ORGANISM: artificial sequence
<220> FEATURE:
<223> OTHER INFORMATION: synthetic peptide

<400> SEQUENCE: 2

Gln Gln Leu Tyr Ser Thr Pro Tyr Thr
1               5

<210> SEQ ID NO 3
<211> LENGTH: 8
<212> TYPE: PRT
<213> ORGANISM: artificial sequence
<220> FEATURE:
<223> OTHER INFORMATION: synthetic peptide

<400> SEQUENCE: 3

Gly Tyr Thr Phe Thr Asn Tyr Gly
1               5

<210> SEQ ID NO 4
<211> LENGTH: 8
<212> TYPE: PRT
<213> ORGANISM: artificial sequence
<220> FEATURE:
<223> OTHER INFORMATION: synthetic peptide

<400> SEQUENCE: 4

Ile Asn Thr Asn Thr Gly Glu Pro
1               5

<210> SEQ ID NO 5
<211> LENGTH: 10
<212> TYPE: PRT
<213> ORGANISM: artificial sequence
<220> FEATURE:
<223> OTHER INFORMATION: synthetic peptide

<400> SEQUENCE: 5

Ala Arg Leu Trp Tyr Leu Tyr Phe Asp Val
1               5                   10

<210> SEQ ID NO 6
<211> LENGTH: 6
<212> TYPE: PRT
<213> ORGANISM: artificial sequence
<220> FEATURE:
<223> OTHER INFORMATION: synthetic peptide

<400> SEQUENCE: 6

Gln Ser Phe Ser Asn Asn
1               5

<210> SEQ ID NO 7
<211> LENGTH: 9
<212> TYPE: PRT
<213> ORGANISM: artificial sequence
<220> FEATURE:
<223> OTHER INFORMATION: synthetic peptide

<400> SEQUENCE: 7

Gln Gln Ser Asn Ser Trp Pro Leu Thr
```

```
1               5
```

<210> SEQ ID NO 8
<211> LENGTH: 8
<212> TYPE: PRT
<213> ORGANISM: artificial sequence
<220> FEATURE:
<223> OTHER INFORMATION: synthetic peptide

<400> SEQUENCE: 8

```
Gly Tyr Thr Phe Thr Asn Tyr Gly
1               5
```

<210> SEQ ID NO 9
<211> LENGTH: 8
<212> TYPE: PRT
<213> ORGANISM: artificial sequence
<220> FEATURE:
<223> OTHER INFORMATION: synthetic peptide

<400> SEQUENCE: 9

```
Ile Asn Thr Asn Thr Gly Glu Pro
1               5
```

<210> SEQ ID NO 10
<211> LENGTH: 10
<212> TYPE: PRT
<213> ORGANISM: artificial sequence
<220> FEATURE:
<223> OTHER INFORMATION: synthetic peptide

<400> SEQUENCE: 10

```
Ala Arg Leu Trp Tyr Leu Tyr Phe Asp Val
1               5                   10
```

<210> SEQ ID NO 11
<211> LENGTH: 107
<212> TYPE: PRT
<213> ORGANISM: artificial sequence
<220> FEATURE:
<223> OTHER INFORMATION: synthetic polypeptide

<400> SEQUENCE: 11

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Arg
            20                  25                  30

Leu Ala Trp Tyr Gln Gln Lys Pro Gly Lys Ser Pro Gln Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Tyr
                85                  90                  95

Thr Phe Gly Gly Gly Thr Lys Leu Glu Ile Lys
            100                 105
```

<210> SEQ ID NO 12
<211> LENGTH: 117
<212> TYPE: PRT
<213> ORGANISM: artificial sequence
<220> FEATURE:
<223> OTHER INFORMATION: synthetic polypeptide

<400> SEQUENCE: 12

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Asn Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Trp Tyr Leu Tyr Phe Asp Val Trp Gly Ala Gly Thr Thr
            100                 105                 110

Val Thr Val Ser Ser
            115

<210> SEQ ID NO 13
<211> LENGTH: 107
<212> TYPE: PRT
<213> ORGANISM: artificial sequence
<220> FEATURE:
<223> OTHER INFORMATION: synthetic polypeptide

<400> SEQUENCE: 13

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Phe Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Lys Phe Thr Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105

<210> SEQ ID NO 14
<211> LENGTH: 117
<212> TYPE: PRT
<213> ORGANISM: artificial sequence
<220> FEATURE:
<223> OTHER INFORMATION: synthetic polypeptide

<400> SEQUENCE: 14

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Asn Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Leu Trp Tyr Leu Tyr Phe Asp Val Trp Gly Ala Gly Thr Thr
            100                 105                 110

Val Thr Val Ser Ser
        115

<210> SEQ ID NO 15
<211> LENGTH: 321
<212> TYPE: DNA
<213> ORGANISM: artificial sequence
<220> FEATURE:
<223> OTHER INFORMATION: synthetic polynucleotide

<400> SEQUENCE: 15
gacattcaga tgacccagtc tcctgcctcc cagtctgcat ctctgggaga aagtgtcacc      60
atcacatgcc tggcaagtca gaccattggt acacggttag catggtatca gcagaaacca     120
gggaaatctc ctcagctcct gatttatgca gcaaccaggt tggcagatgg ggtcccatca     180
aggttcagtg gtagtggatc tggcacaaaa ttttctttca agatcagcag cctacaggct     240
gaagattttg taagttatta ctgtcaacaa ctttacagta ctccgtacac gttcggaggg     300
gggaccaagc tggaaataaa a                                                321

<210> SEQ ID NO 16
<211> LENGTH: 351
<212> TYPE: DNA
<213> ORGANISM: artificial sequence
<220> FEATURE:
<223> OTHER INFORMATION: synthetic polynucleotide

<400> SEQUENCE: 16
cagatccagt tggtgcagtc tggacctgag ctgaagaagc ctggagagac agtcaagatc      60
tcctgcaagg cttctgggta taccttcaca aactatggaa tgaactgggt aaaccaggct     120
ccaggaaagg gtttaaagtg gatgggctgg ataaacacca cactggaga gccaacatat      180 gctgaagagt tcaagggacg gtttgccttc tctttggaaa cctctgccag cactgcctat     240
ttgcagatca caacctcaa aaatgaggac acggctacat atttctgtgc aagattgtgg      300
tacctgtact cgatgtctg ggcgcaggg accacggtca ccgtctcctc a                 351

<210> SEQ ID NO 17
<211> LENGTH: 322
<212> TYPE: DNA
<213> ORGANISM: artificial sequence
<220> FEATURE:
<223> OTHER INFORMATION: synthetic polynucleotide

<400> SEQUENCE: 17
gatattgtgc taactcagtc tccagccacc ctgtctgtga ctccaggaga tagcgtcagt      60
ctttcctgca gggccagcca aagttttagc aacaacctac actggtatca acaaaaatca     120
catgagtctc caaggcttct catcaagtat gcttcccagt ccatctctgg atcccctcc      180 aagttcactg gcagtggatc aggacagat ttcactctca gtatcaacag tgtggagact      240
gaagattttg gaatgtattt ctgtcaacag agtaacagct ggcctctcac gttcggtgct     300
gggaccaagc tggagttgaa ac                                               322
```

```
<210> SEQ ID NO 18
<211> LENGTH: 351
<212> TYPE: DNA
<213> ORGANISM: artificial sequence
<220> FEATURE:
<223> OTHER INFORMATION: synthetic polynucleotide

<400> SEQUENCE: 18
cagatccagt tggtgcagtc tggacctgag ctgaagaagc ctggagagac agtcaagatc      60
tcctgcaagg cttctgggta taccttcaca aactatggaa tgaactgggt aaaccaggct     120
ccaggaaagg gtttaaagtg gatgggctgg ataaacacca acactggaga gccaacatat     180
gctgaagagt tcaagggacg gtttgccttc tctttggaaa cctctgccag cactgcctat     240
ttgcagatca caacctcaa aaatgaggac acggctacat atttctgtgc aagattgtgg      300
tacctgtact tcgatgtctg gggcgcaggg accacggtca ccgtctcctc a              351
```